(12) United States Patent
Eagle et al.

(10) Patent No.: US 10,456,046 B2
(45) Date of Patent: Oct. 29, 2019

(54) DEVICE AND METHOD FOR HEMORRHAGE DETECTION AND GUIDED RESUSCITATION AND APPLICATIONS OF SAME

(71) Applicant: Vanderbilt University, Nashville, TN (US)

(72) Inventors: Susan Eagle, Nashville, TN (US); Colleen Brophy, Nashville, TN (US); Kyle Hocking, Nashville, TN (US); Franz Baudenbacher, Franklin, TN (US); Richard Boyer, Nashville, TN (US)

(73) Assignee: Vanderbilt University, Nashville, TN (US)

( * ) Notice: Subject to any disclaimer, the term of this patent is extended or adjusted under 35 U.S.C. 154(b) by 51 days.

(21) Appl. No.: 15/525,748

(22) PCT Filed: Nov. 13, 2015

(86) PCT No.: PCT/US2015/060697
§ 371 (c)(1),
(2) Date: May 10, 2017

(87) PCT Pub. No.: WO2016/077765
PCT Pub. Date: May 19, 2016

(65) Prior Publication Data
US 2017/0332919 A1    Nov. 23, 2017

Related U.S. Application Data

(63) Continuation-in-part of application No. 14/853,504, filed on Sep. 14, 2015.
(Continued)

(51) Int. Cl.
*A61B 6/02* (2006.01)
*A61B 5/02* (2006.01)
(Continued)

(52) U.S. Cl.
CPC ...... *A61B 5/02028* (2013.01); *A61B 5/02007* (2013.01); *A61B 5/02042* (2013.01);
(Continued)

(58) Field of Classification Search
CPC .............. A61B 5/0002; A61B 5/02007; A61B 5/02028; A61B 5/02042; A61B 5/02438;
(Continued)

(56) References Cited

U.S. PATENT DOCUMENTS

| 7,596,412 B1* | 9/2009 | Kroll | A61B 5/02028 607/18 |
| 2004/0193068 A1* | 9/2004 | Burton | A61B 5/0476 600/544 |

(Continued)

FOREIGN PATENT DOCUMENTS

| CN | 103049631 A | 4/2013 |
| WO | WO 98/46126 A1 | 10/1998 |

(Continued)

OTHER PUBLICATIONS

Langley, P. et al., "Computer Algorithm for Tracking ECG Spectral Dynamics in Ventricular Tachyarrhythmias," Computers in Cardiology 2009; 36:329-332.

*Primary Examiner* — Carl H Layno
*Assistant Examiner* — Michael J Lau
(74) *Attorney, Agent, or Firm* — McDonnell Boehnen Hulbert & Berghoff LLP

(57) ABSTRACT

Aspects of the invention relates to systems and methods for detecting volume status, volume overload, dehydration, hemorrhage and real time assessment of resuscitation, as well as organ failure including but not limited cardiac, renal, and hepatic dysfunction, of a living subject using non-invasive vascular analysis (NIVA). In one embodiment, a non-invasive device, which includes at least one sensor, is (Continued)

used to acquire vascular signals from the living subject in real time. The vascular signals are sent to a controller, which processes the vascular signals to determine at least one hemodynamic parameter, such as the volume status of the living subject. In certain embodiments, the vascular signals are processed by a spectral fast Fourier transform (FFT) analysis to obtain the peripheral vascular signal frequency spectrum, and the volume status of the living subject may be determined by comparing amplitudes of the peaks of the peripheral vascular signal frequency spectrum.

22 Claims, 14 Drawing Sheets

Related U.S. Application Data

(60) Provisional application No. 62/079,367, filed on Nov. 13, 2014, provisional application No. 62/049,829, filed on Sep. 12, 2014.

(51) Int. Cl.
*A61B 5/00* (2006.01)
*A61B 5/0215* (2006.01)
*A61B 5/024* (2006.01)
*A61B 5/08* (2006.01)

(52) U.S. Cl.
CPC .......... *A61B 5/02152* (2013.01); *A61B 5/681* (2013.01); *A61B 5/7257* (2013.01); *A61B 5/0002* (2013.01); *A61B 5/02438* (2013.01); *A61B 5/0816* (2013.01); *A61B 5/4875* (2013.01); *A61B 5/7221* (2013.01)

(58) Field of Classification Search
CPC . A61B 5/02152; A61B 5/0816; A61B 5/4875; A61B 5/681; A61B 5/7221; A61B 5/7257; G01R 23/00
USPC ........................................................ 600/301
See application file for complete search history.

(56) References Cited

U.S. PATENT DOCUMENTS

| 2005/0177051 | A1* | 8/2005 | Almen | A61B 5/02405 600/509 |
|---|---|---|---|---|
| 2007/0060827 | A1* | 3/2007 | Kobayashi | A61B 5/02416 600/500 |
| 2008/0064965 | A1* | 3/2008 | Jay | A61B 5/02028 600/484 |
| 2008/0067132 | A1* | 3/2008 | Ross | A61B 5/02007 210/739 |
| 2008/0294019 | A1* | 11/2008 | Tran | A61B 5/0006 600/301 |
| 2009/0005696 | A1* | 1/2009 | Riftine | A61B 5/02405 600/515 |
| 2010/0081942 | A1* | 4/2010 | Huiku | G16H 40/60 600/483 |
| 2010/0222655 | A1 | 9/2010 | Starr et al. | |
| 2011/0077486 | A1 | 3/2011 | Watson et al. | |
| 2011/0112379 | A1* | 5/2011 | Li | A61B 5/14552 600/300 |
| 2011/0199613 | A1* | 8/2011 | Iijima | A61B 5/02438 356/445 |
| 2011/0208016 | A1 | 8/2011 | Bombardini | |
| 2012/0123232 | A1* | 5/2012 | Najarian | A61B 5/0022 600/345 |
| 2012/0271554 | A1* | 10/2012 | Shelley | A61B 5/02 702/19 |
| 2012/0296219 | A1* | 11/2012 | Chon | A61B 5/02042 600/479 |
| 2013/0018239 | A1* | 1/2013 | Lisogurski | A61B 5/0004 600/322 |
| 2013/0165802 | A1* | 6/2013 | Dalal | A61B 5/7239 600/486 |
| 2013/0184594 | A1* | 7/2013 | Shelley | A61B 5/02007 600/484 |
| 2013/0226009 | A1* | 8/2013 | Mestek | A61B 5/02042 600/479 |
| 2013/0261468 | A1* | 10/2013 | Semler | A61B 5/4875 600/473 |
| 2013/0267858 | A1* | 10/2013 | Berkow | A61B 5/02028 600/479 |
| 2013/0274567 | A1* | 10/2013 | Grosser | A61B 5/07 600/301 |
| 2013/0303921 | A1* | 11/2013 | Chu | A61B 5/0059 600/473 |
| 2013/0303923 | A1* | 11/2013 | Lerner | A61B 5/02208 600/492 |
| 2013/0345568 | A1* | 12/2013 | Mestha | A61B 5/7235 600/473 |
| 2014/0073931 | A1* | 3/2014 | Galea | A61B 5/021 600/473 |
| 2014/0121540 | A1* | 5/2014 | Raskin | A61B 5/6898 600/479 |
| 2014/0288390 | A1* | 9/2014 | Hong | A61B 5/02427 600/301 |

FOREIGN PATENT DOCUMENTS

| WO | WO 01/58345 A1 | 8/2001 |
|---|---|---|
| WO | WO 2009/038431 A2 | 3/2009 |
| WO | WO 2013/109389 A1 | 7/2013 |

* cited by examiner

300

300'

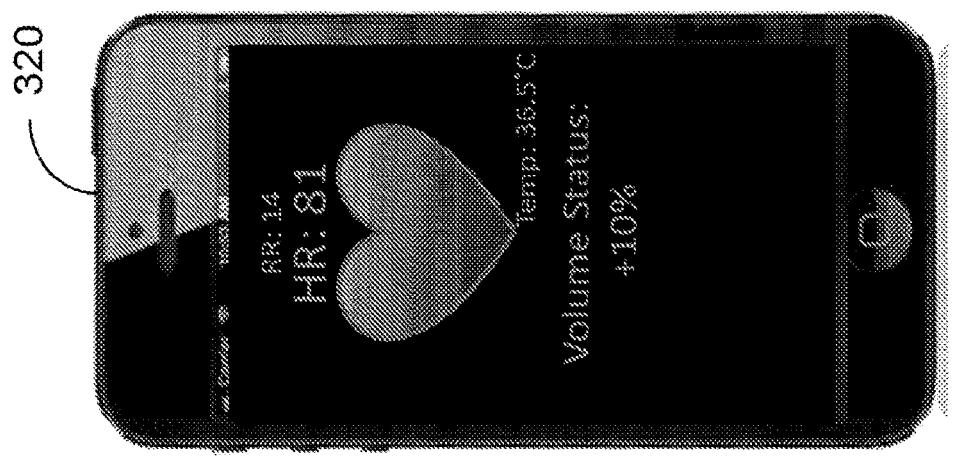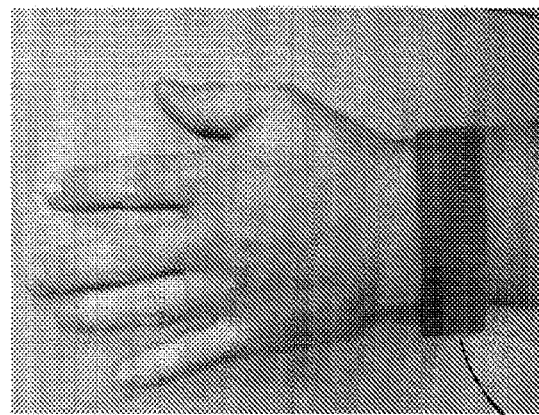
FIG. 3C

DEVICE AND METHOD FOR HEMORRHAGE DETECTION AND GUIDED RESUSCITATION AND APPLICATIONS OF SAME

CROSS-REFERENCE TO RELATED PATENT APPLICATIONS

This application is a U.S. national phase of International Application No. PCT/US2015/060697, filed on Nov. 13, 2015, which claims priority to and the benefit of, pursuant to 35 U.S.C. § 119(e), U.S. provisional patent application Ser. No. 62/079,367, filed Nov. 13, 2014, entitled "DEVICE AND METHOD FOR HEMORRHAGE DETECTION AND GUIDED RESUSCITATION AND APPLICATIONS OF SAME," by Susan S. Eagle, Colleen Brophy, Kyle Mitchell Hocking, Franz Baudenbacher and Richard Boyer, the above disclosures of which are incorporated herein in their entireties by reference.

This application is a U.S. national phase of International Application No. PCT/US2015/060697, filed on Nov. 13, 2015, which is also a continuation-in-part of U.S. patent application Ser. No. 14/853,504, filed Sep. 14, 2015, entitled "HYPOVOLEMIA/HYPERVOLEMIA DETECTION USING PERIPHERAL INTRAVENOUS WAVEFORM ANALYSIS (PIVA) AND APPLICATIONS OF SAME," by Susan S. Eagle, Colleen Brophy, Kyle Mitchell Hocking, Franz Baudenbacher and Richard Boyer, which itself claims priority to and the benefit of, pursuant to 35 U.S.C. § 119(e), U.S. provisional patent application Ser. No. 62/049,829, filed Sep. 12, 2014, entitled "METHOD FOR HARMONIC ANALYSIS OF PERIPHERAL VENOUS PRESSURE WAVEFORMS AND APPLICATIONS OF SAME," by Susan S. Eagle, Colleen Brophy, Kyle Mitchell Hocking, Franz Baudenbacher and Richard Boyer, all the above disclosures of which are incorporated herein in their entireties by reference.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the n-th reference cited in the reference list. For example, [1] represents the first reference cited in the reference list, namely, Hubetamann B, Lefering R, Taeger G, et al., *Influence of prehospital fluid resuscitation on patients with multiple injuries in hemorrhagic shock in patients from the DGU trauma registry*. Journal of emergencies, trauma, and shock 2011; 4:465-71.

FIELD OF THE INVENTION

The present invention relates generally to detection of volume overload, dehydration, hemorrhage and real time assessment of resuscitation of a living subject, and more specifically, the present invention relates to systems and methods of using non-invasive vascular analysis (NIVA) to assess hemodynamic parameters, such as blood volume status of a living subject, and applications of the same.

BACKGROUND OF THE INVENTION

Fluid overload detection is difficult, from administering excessive fluids and or pathologic conditions. Fluid overload leads to increased morbidity and mortality. While fluid administration is paramount for maintaining tissue perfusion and preventing hemodynamic collapse in the hemorrhaging patients, excessive fluid administration results in decreased organ perfusion, acidosis, coagulopathy, and increased mortality [6, 18, 19]. Studies dating back to World War II have emphasized the importance of restricting fluid therapy prior to definitive surgical control [20]. Nonetheless, fluid resuscitation remains largely unguided due to inadequate hemodynamic monitoring and decision-support mechanisms [9]. Standard vital sign monitoring fails to detect euvolemia or hypervolemia during resuscitation, resulting in unguided, excessive fluid administration. Further, invasive monitoring is often not feasible. This leaves a critical need for a point-of-care monitor for real-time guided fluid resuscitation. Similarly, patients with congestive heart failure and renal failure often have fluid overload, leading to repeat hospitalizations [21]. Often this is not detected until after patients have symptomatic pulmonary edema and shortness of breath. Therefore there is an unmet need for a non-invasive volume status monitor in the outpatient setting to detect fluid overload in patients with cardiac and renal failure prior to the development of symptoms and need for hospitalization.

Further, hemorrhagic shock remains the leading preventable cause of death in the casualty care setting [2, 3]. Survival is contingent upon early recognition of hemorrhage, appropriate triage, and goal-directed transfusion therapy [4, 5]. Timely damage control surgery (DCS) and restrictive fluid resuscitation (RFR) have been shown to significantly improve mortality [6]. However, recognition of subclinical hemorrhage and proper fluid resuscitation has remained elusive, resulting in delayed triage and poor management of patients with acute blood loss [7].

Subclinical and ongoing blood loss is difficult to detect. Often, continuous occult bleeding is not recognized until the onset of hemorrhagic shock and hemodynamic collapse, particularly in young, healthy patients with good compensatory mechanisms [8, 9]. Unrecognized hemorrhage leads to delayed triage and DCS, resulting in preventable end-organ damage [10-12]. Standard vital sign monitoring, including heart rate and blood pressure, fails to detect hemorrhage prior to end-organ damage [7, 13]. Arterial-based methods such as pulse pressure variation (PPV), stroke volume variation (SVV), and plethysmographic wave respiratory variation can only predict fluid responsiveness but do not directly measure volume status [14, 15]. Further, PPV and SVV depend on changes in heart-lung interactions via mechanical ventilation for detecting hypovolemia [14, 16]. This critical limitation renders arterial-based monitors ineffective for detecting hypovolemia in the spontaneously breathing patient [17]. There is an acute unmet need for a point of care monitor that can measure volume status in patients, detect early subclinical hemorrhage and warn of impending hemodynamic collapse. Optimal patient care and measurements of volume status is particularly challenging in the casualty care, emergency response or rural setting. The casualty care or rural setting poses several unique challenges—austere environments, limited access to healthcare providers, ineffective monitoring devices, and lack of remote monitoring. There is a critical need for a rugged, real-time mobile monitoring and decision support mechanisms to improve survival in these environments. Therefore, there is a critical unmet need for a cost effective point of care device to assess the fluid status in patients for hemorrhage detection, goal-directed resuscitation, dehydration, fluid overload, and appropriate triage to improve mortality and need for hospitalization.

Therefore, a heretofore unaddressed need exists in the art to address the aforementioned deficiencies and inadequacies.

SUMMARY OF THE INVENTION

In one aspect, the present invention relates to a non-invasive vascular analysis (NIVA) system for detecting or monitoring intravascular volume status, volume overload, dehydration, hemorrhage, cardiac/renal/hepatic function, pulmonary embolism, vascular endothelial function, vascular compliance, and real time assessment of resuscitation of a living subject. In certain embodiments, the system includes: at least one sensor, configured to acquire, continuously for a time period from $T_0$ to $T_2$, vascular signals from at least one peripheral vein, artery or perfused tissue of the living subject in real time, wherein the time period is divided into a first time period from $T_0$ to $T_1$, and a second time period from $T_1$ to $T_2$; and a processing device communicatively coupled to the at least one sensor, configured to receive the vascular signals transmitted from the at least one sensor, and perform a spectral analysis on the vascular signals. In certain embodiments, the spectral analysis comprises the steps of: processing the vascular signals acquired at the first time period to obtain a baseline peripheral vascular signal frequency spectrum; obtaining a plurality of baseline peaks $\{B_{N-1}\}$ on the baseline peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$; processing the vascular signals acquired at the second time period to obtain a peripheral vascular signal frequency spectrum; obtaining a plurality of peaks $\{P_{N-1}\}$ on the peripheral vascular pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining at least one hemodynamic parameter of the living subject at the second time period by comparing amplitudes of the peaks $\{P_{N-1}\}$ to those of the baseline peaks $\{B_{N-1}\}$ respectively.

In certain embodiments, the vascular signals are processed by a spectral fast Fourier transform (FFT) analysis to obtain the baseline peripheral vascular signal frequency spectrum and the peripheral vascular signal frequency spectrum, respectively.

In certain embodiments, each of the at least one sensor is a piezoelectric sensor, a resistive pressure/force sensor, an optical wavelength selective reflectance or absorbance measurement system, a tonometer, an ultrasound, bioimpedence, plethysmography, or pressure transducer, or any combination thereof.

In certain embodiments, the at least one sensor and the processing device form a non-invasive device, wherein the non-invasive device is a wearable band, an adhesive, or an attachment being in contact with a surface of skin of the living subject overlying the at least one peripheral vein, artery or perfused tissue.

In certain embodiments, the processing device includes: a processor configured to receive the vascular signals transmitted from the at least one sensor, wherein the at least one sensor and the processor form the non-invasive device; and a monitoring device configured to communicate with the processor via a wireless protocol to receive the vascular signals, and to perform the spectral analysis for monitoring condition of the living subject in real time. In one embodiment, the monitoring device is further configured to display results of the spectral analysis on the non-invasive device. In certain embodiments, the monitoring device is configured to communicate with the processor via a wireless protocol, and is a smartphone, a tablet computing device, a laptop computing device, a desktop computing device, or any combination thereof.

In certain embodiments, the at least one hemodynamic parameter of the living subject comprises information of volume status, heart rate, heart rate variability, oximetry, blood pressure, pulse pressure variability, temperature, and respiratory rate of the living subject.

In certain embodiments, the volume status of the living subject at the second time period indicates hypovolemia or hypervolemia when amplitude changes greater than a threshold are detected from the baseline peaks $\{B_{N-1}\}$ to the peaks $\{P_{N-1}\}$.

In certain embodiments, the plurality of peaks $\{P_{N-1}\}$ comprises a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$. In certain embodiments, the first peak $P_0$ corresponding to the first frequency $F_0$ is associated with a respiratory rate of the living subject; the second peak $P_1$ corresponding to the second frequency $F_1$ is associated with a heart rate of the living subject; and the third peak $P_2$ corresponding to the third frequency $F_2$ and the fourth peak $P_3$ corresponding to the fourth frequency $F_3$ are associated with harmonics of the living subject.

Another aspect of the present invention relates to a NIVA system for detecting or monitoring intravascular volume status, volume overload, dehydration, hemorrhage, cardiac/renal/hepatic function, pulmonary embolism, vascular endothelial function, vascular compliance, and real time assessment of resuscitation of a living subject. In certain embodiments, the system includes: a non-invasive device, comprising: at least one sensor, configured to acquire vascular signals from the living subject in real time; and a controller communicatively coupled to the at least one sensor, configured to receive the vascular signals transmitted from the at least one sensor, and process the vascular signals to determine at least one hemodynamic parameter of the living subject.

In certain embodiments, each of the at least one sensor is a piezoelectric sensor, a resistive pressure/force sensor, an optical wavelength selective reflectance or absorbance measurement system, a tonometer, an ultrasound, bioimpedence, plethysmography, or pressure transducer, or any combination thereof.

In certain embodiments, the non-invasive device is a wearable band, an adhesive, or an attachment being in contact with a surface of skin of the living subject overlying at least one peripheral vein, artery or perfused tissue, wherein the at least one sensor is configured to acquire the vascular signals from the at least one peripheral vein, artery or perfused tissue.

In certain embodiments, the controller is a microcontroller or a processor.

In certain embodiments, the system further includes a monitoring device configured to communicate with the controller to receive the vascular signals and the at least one hemodynamic parameter, for monitoring condition of the living subject in real time. In certain embodiments, the monitoring device is a smartphone, a tablet computing device, a laptop computing device, a desktop computing device, or any combination thereof. In one embodiment, the monitoring device communicates with the controller via a wireless protocol.

In certain embodiments, the monitoring device or the controller performs a spectral analysis and utilizes algorithms on the vascular signals from the at least one sensor to compute information of the at least one hemodynamic parameter, and display the information graphically.

In certain embodiments, the at least one hemodynamic parameter comprises volume status, heart rate, heart rate variability, oximetry, blood pressure, pulse pressure variability, temperature, and respiratory rate of the living subject.

In certain embodiments, the at least one sensor is configured to acquire, continuously for a time period from $T_0$ to $T_2$, the vascular signals from the at least one peripheral vein, artery or perfused tissue of the living subject, wherein the time period is divided into a first time period from $T_0$ to $T_1$, and a second time period from $T_1$ to $T_2$.

In certain embodiments, the spectral analysis includes the steps of: processing the vascular signals acquired at the first time period to obtain a baseline peripheral vascular signal frequency spectrum; obtaining a plurality of baseline peaks $\{B_{N-1}\}$ on the baseline peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$; processing the vascular signals acquired at the second time period to obtain a peripheral vascular signal frequency spectrum; obtaining a plurality of peaks $\{P_{N-1}\}$ on the peripheral vascular pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining the volume status of the living subject at the second time period by comparing amplitudes of the peaks $\{P_{N-1}\}$ to those of the baseline peaks $\{B_{N-1}\}$ respectively, wherein the volume status of the living subject at the second time period indicates hypovolemia or hypervolemia when amplitude changes greater than a threshold are detected from the baseline peaks $\{B_{N-1}\}$ to the peaks $\{P_{N-1}\}$.

In certain embodiments, the vascular signals are processed by a spectral fast Fourier transform (FFT) analysis to obtain the baseline peripheral vascular signal frequency spectrum and the peripheral vascular signal frequency spectrum, respectively.

In certain embodiments, the plurality of peaks $\{P_{N-1}\}$ comprises a first peak $P_0$ corresponding to a first frequency $F_0$ and a second peak $P_1$ corresponding to a second frequency $F_1$. In one embodiment, the first peak $P_0$ corresponding to the first frequency $F_0$ is associated with a respiratory rate of the living subject; and the second peak $P_1$ corresponding to the second frequency $F_1$ is associated with a heart rate of the living subject.

In certain embodiments, the plurality of peaks $\{P_{N-1}\}$ further comprises a third peak $P_2$ corresponding to a third frequency $F_2$ and a fourth peak $P_3$ corresponding to a fourth frequency $F_3$; and the third peak $P_2$ corresponding to the third frequency $F_2$ and the fourth peak $P_3$ corresponding to the fourth frequency $F_3$ are associated with harmonics of the living subject.

In a further aspect of the present invention, a non-invasive device for performing a NIVA includes: at least one sensor, configured to acquire vascular signals from the living subject in real time; and a controller communicatively coupled to the at least one sensor, configured to receive the vascular signals transmitted from the at least one sensor, and process the vascular signals to determine at least one hemodynamic parameter of the living subject.

A further aspect of the present invention relates to a non-invasive method for detecting or monitoring intravascular volume status, volume overload, dehydration, hemorrhage, cardiac/renal/hepatic function, pulmonary embolism, vascular endothelial function, vascular compliance, and real time assessment of resuscitation of a living subject, which includes: acquiring, from at least one peripheral vein, artery or perfused tissue of the living subject using a non-invasive device, vascular signals in real time; and processing the acquired vascular signals to obtain a peripheral vascular pressure frequency spectrum to determine at least one hemodynamic parameter of the living subject.

In certain embodiments, the non-invasive device is a wearable band, an adhesive, or an attachment being in contact with a surface of skin of the living subject overlying the at least one peripheral vein, artery or perfused tissue.

In certain embodiments, the non-invasive device includes: at least one sensor, configured to acquire the vascular signals in real time; and a controller communicatively coupled to the at least one sensor, configured to receive the vascular signals transmitted from the at least one sensor, and perform a spectral analysis on the vascular signals to determine the at least one hemodynamic parameter of the living subject.

In certain embodiments, the at least one hemodynamic parameter comprises volume status, heart rate, heart rate variability, oximetry, blood pressure, pulse pressure variability, temperature, and respiratory rate of the living subject.

In certain embodiments, the at least one sensor is configured to acquire, continuously for a time period from $T_0$ to $T_2$, the vascular signals from the at least one peripheral vein, artery or perfused tissue of the living subject, wherein the time period is divided into a first time period from $T_0$ to $T_1$, and a second time period from $T_1$ to $T_2$. In certain embodiments, the spectral analysis includes: processing the vascular signals acquired at the first time period to obtain a baseline peripheral vascular signal frequency spectrum; obtaining a plurality of baseline peaks $\{B_{N-1}\}$ on the baseline peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$; processing the vascular signals acquired at the second time period to obtain a peripheral vascular signal frequency spectrum; obtaining a plurality of peaks $\{P_{N-1}\}$ on the peripheral vascular pressure frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining the volume status of the living subject at the second time period by comparing amplitudes of the peaks $\{P_{N-1}\}$ to those of the baseline peaks $\{B_{N-1}\}$ respectively, wherein the volume status of the living subject at the second time period indicates hypovolemia or hypervolemia when amplitude changes greater than a threshold are detected from the baseline peaks $\{B_{N-1}\}$ to the peaks $\{P_{N-1}\}$.

In certain embodiments, the vascular signals are processed by a spectral fast Fourier transform (FFT) analysis to obtain the baseline peripheral vascular signal frequency spectrum and the peripheral vascular signal frequency spectrum, respectively.

In certain embodiments, the plurality of peaks $\{P_{N-1}\}$ comprises a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$; the first peak $P_0$ corresponding to the first frequency $F_0$ is associated with a respiratory rate of the living subject; the second peak $P_1$ corresponding to the second frequency $F_1$ is associated with a heart rate of the living subject; and the third peak $P_2$ corresponding to the third frequency $F_2$ and the fourth peak $P_3$ corresponding to the fourth frequency $F_3$ are associated with harmonics of the living subject.

A further aspect of the present invention may relate to a NIVA system for detecting or monitoring intravascular volume status, volume overload, dehydration, hemorrhage, cardiac/renal/hepatic function, pulmonary embolism, vascular endothelial function, vascular compliance, and real time assessment of resuscitation of a living subject by performing the method as described above.

In a further aspect, the present invention relates to a mobile device, storing a mobile application containing instructions which, when executed by one or more processors of the mobile device, cause a system to perform the method as described above.

In a further aspect, the present invention relates to a non-transitory computer-readable medium storing instructions which, when executed by one or more processors, cause a system to perform the method as described above.

One further aspect of the present invention relates to a system, which includes the NIVA system as described above, and an administration device communicatively connected to the NIVA system, for controlling, based on the at least one hemodynamic parameter of the living subject provided by the NIVA system, administration of a drug or fluid to the living subject, or for controlling a rate or ultrafiltration of fluid removal from the living subject. In certain embodiments, the administration device comprises an intravenous (IV) pump for controlling the administration the drug or fluid. In certain embodiments, the administration device is configured to control the administration of the drug or fluid to the living subject based on the at least one hemodynamic parameter of the living subject to maintain a specific physiological condition of the living subject. For example, one particular physiological condition may be euvolemia, and the controlling of the administration of fluid or drug may be conducted to prevent over-resuscitation.

These and other aspects of the present invention will become apparent from the following description of the preferred embodiments taken in conjunction with the following drawings, although variations and modifications thereof may be affected without departing from the spirit and scope of the novel concepts of the disclosure.

BRIEF DESCRIPTION OF THE DRAWINGS

The accompanying drawings illustrate one or more embodiments of the invention and, together with the written description, serve to explain the principles of the invention. Wherever possible, the same reference numbers are used throughout the drawings to refer to the same or like elements of an embodiment.

FIG. 3C shows Bluetooth communication from a wristband to a smartphone application to determine volume status according to certain embodiments of the present invention.

DETAILED DESCRIPTION OF THE INVENTION

Figure 1:
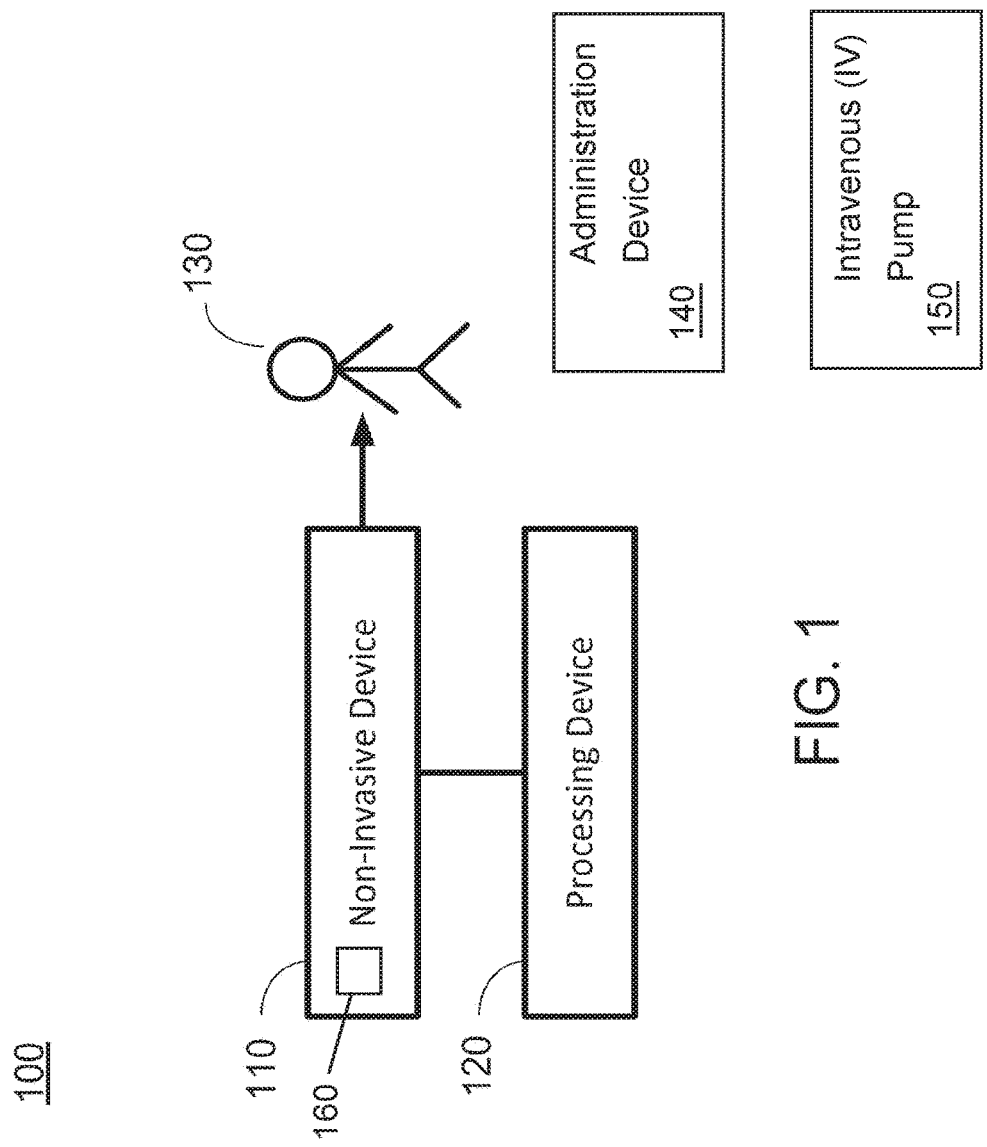
FIG. 1 schematically shows a NIVA system according to certain embodiments of the present invention.

The invention will now be described more fully hereinafter with reference to the accompanying drawings, in which exemplary embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like reference numerals refer to like elements throughout.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term are the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

It will be understood that when an element is referred to as being "on" another element, it can be directly on the other element or intervening elements may be present there between. In contrast, when an element is referred to as being "directly on" another element, there are no intervening elements present. As used herein, the term "and/or" includes any and all combinations of one or more of the associated listed items.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the invention.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising", or "includes" and/or "including" or "has" and/or "having" when used in this specification specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top", may be used herein to describe one element's relationship to another element as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower" can, therefore, encompass both an orientation of "lower" and "upper", depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

As used herein, "around", "about", "substantially" or "approximately" shall generally mean within 20 percent, preferably within 10 percent, and more preferably within 5 percent of a given value or range. Numerical quantities given herein are approximate, meaning that the term "around", "about", "substantially" or "approximately" can be inferred if not expressly stated.

As used herein, the terms "comprise" or "comprising", "include" or "including", "carry" or "carrying", "has/have" or "having", "contain" or "containing", "involve" or "involving" and the like are to be understood to be open-ended, i.e., to mean including but not limited to.

As used herein, the term "non-invasive vascular analysis" or its abbreviation "NIVA" refers to an analysis of the peripheral vascular waveforms measured from a peripheral vein, artery or perfused tissue of a living subject through a non-invasive device.

As used herein, the term "hemodynamic" generally refers to blood movement, and "hemodynamic resuscitation" generally refers to increasing blood movement (or blood pressure) in a patient experiencing symptoms of compensated shock (e.g., based on a "hemodynamic score" or "resuscitation score").

As used herein, the term "hypovolemia" refers to a medical condition of decreased blood volume, and more specifically a decrease in volume of blood plasma. In certain embodiments, hypovolemia stems from loss of blood volume due to hemorrhage, dehydration or intravascular water loss.

As used herein, the term "hypervolemia" refers to a medical condition of fluid overload (i.e., having too much fluid) in the blood. In certain embodiments, hypervolemia stems from compromised regulatory mechanisms for sodium handling, such as congestive heart failure (CHF) or renal failure, or due to iatrogenic fluid administration.

OVERVIEW OF THE INVENTION

The description is now made as to the embodiments of the invention in conjunction with the accompanying drawings. Although various exemplary embodiments of the present invention disclosed herein may be described in the context of one particular type of a sensor for analyzing vascular elements device, which may be implemented as a NIVA system, a point of care (POC) device, a method of using the same, and applications of the same, it should be appreciated that aspects of the present invention disclosed herein are not limited to being used in connection with the systems, devices and methods, and may be practiced in connection with other types of applications without departing from the scope of the present invention disclosed herein.

Non-invasive real time strategies for monitoring and managing volume status of individuals in the injured athletes or the combat casualty setting in, but not limited to trauma, ICU or CHF patients in the civilian setting, diarrheal illnesses, or dehydration are non-existing. Non-invasive vital sign monitors such as blood pressure and heart rate lack sensitivity for detecting early subclinical hemorrhage or compensated substantial hemorrhage. Pulse pressure variation and stroke volume variation, based on arterial waveform analysis, require direct arterial access and are contingent upon delivering positive pressure ventilation, rendering them ineffective for the spontaneously breathing person. In addition, the current gold-standard measurement requires either echocardiography or a pulmonary artery catheter, and both of these measurements have wide variability in their accuracy; standard vital sign monitoring lacks the ability to detect volume status, leading to inadvertent over-administration of fluids during resuscitation. Both of these devices constitute invasive monitoring. Thus, one of the objectives of the invention is to provide a non-invasive device and decision-support algorithm for early hemorrhage detection and guided fluid resuscitation.

In one aspect, the invention relates to a cost effective point of care (POC) device, and more particularly, to a "sensor for analyzing vascular elements" (SAVE) for volume status measurements, early and accurate detection of volume overload, dehydration, and real time assessment of resuscitation. The sensor can be placed non-invasively on the skin overlaying the vasculature of the patient.

In certain aspects, the invention relates to a smart wireless wristband based device and mobile application to alert medical personnel, quantitate intravascular volume status, guide fluid resuscitation, and provide guided decision support for managing patients in a variety of clinical settings. The described device is an innovative POC strategy for detecting hypovolemia including compensated hypovolemic shock, as well as hypervolemia due to a variety of conditions including but not limited to cardiac and renal abnormalities, and guide resuscitation to improve outcomes.

In certain embodiments, a system may include at least one sensor, such as a pressure/force sensitive sensor for detecting a signal from at least one peripheral vein, artery, or combination of vasculature. The system may also include a controller device configured to receive a signal from the pressure/force sensitive sensor. The controller may be used to perform a spectral analysis technique of the time domain data to process the signal to determine a parameter related to cardiac output and combined with other parameters allows for the detection of compensated shock. In one embodiment, the spectral analysis technique may be a Fourier transformation. Once the Fourier spectrum is generated, the amplitude or power of the wave that corresponds to the harmonic frequencies of the heart rate or any other parameter's amplitude or power is measured at the fundamental and higher order frequencies. The amplitudes and/or powers are input into the algorithm that weights each resonant frequency and outputs a measurement of the volume status or any other parameter related to circulation. In certain embodiments, additional inputs may also be required, including but not limited to the following: age, weight, gender, and height, these variables may be input into the algorithm to determine a more accurate depiction of the patient's physiological condition. The non-invasive peripheral vascular waveform analysis may include, but not limited to, Fourier transform of the pressure/force transducer signal or associated signals. Based on the analysis, the volume status and/or other hemodynamic parameters, e.g., potentially additional vitals, may be determined to generate a resuscitation score.

In certain embodiments, a system and method have been developed for determining volume status using venous and peripheral vascular waveform and/or pressure analysis. This approach signifies a major paradigm shift from conventional arterial-based methods for determining intravascular volume status. The non-invasive venous and peripheral vascular waveform analysis overcomes many critical barriers associated with standard arterial-based monitoring. The inventors first discovered that peripheral intravenous waveform analysis obtained via a pressure transducer in a standard intravenous (IV) catheter may be used to detect hemorrhage in humans and porcine models. However, the utilization of the pressure transducer in a catheter is limited in the field. Therefore, the inventors sought to develop a non-invasive device for professional and consumer market and to obviate the immediate need for skilled medical personnel and intravenous catheter insertion. Further, the non-invasive device can be applied to patients prior to interventions or maneuvers, establishing a baseline euvolemic state thereby detecting deviations from euvolemia and increasing the sensitivity of hemorrhage detection or volume status changes. The inventors capitalized on advances in low-cost, high-gain, off-the-shelf piezoelectric sensor technologies to detect non-invasive pulse waveforms and started to develop a non-invasive device.

Certain aspects of the present invention relate to a NIVA system for detecting or monitoring intravascular volume status, volume overload, dehydration, hemorrhage, cardiac/renal/hepatic function, pulmonary embolism, vascular endothelial function, vascular compliance, and real time assessment of resuscitation of a living subject, and the a non-invasive device thereof. FIG. 1 schematically shows a NIVA system according to certain embodiments of the present invention. As shown in FIG. 1, the NIVA system 100 includes a non-invasive device 110 and a processing device 120. The processing device 120 is communicatively connected to the non-invasive device 110. In certain embodiments, the connection between the non-invasive device 110 and the processing device 120 may be through a network, which may be implemented by a wired connection or a wireless connection. Examples of the network may include without being limited to, a local area network (LAN), a wide area network (WAN), the Internet, or any other types of network. FIG. 1 also shows a subject 130, an administration device 140, an intravenous (IV) pump 150, and a sensor 160.

In certain embodiments, the non-invasive device 110 may include at least one sensor, which is configured to acquire vascular signals from the living subject in real time. In certain embodiments, the living subject may be a human being, or may be other animals. In one embodiment, the living subject may be a human patient or an animal patient. The processing device 120 is configured to receive the vascular signals transmitted from the at least one sensor, and perform a spectral analysis on the vascular signals in order to determine at least one hemodynamic parameter of the living subject. In certain embodiments, the vascular signals being acquired by the at least one sensor may be transmitted to a controller communicatively coupled to the at least one sensor. The controller is configured to receive the vascular signals transmitted from the at least one sensor, and process the vascular signals to determine at least one hemodynamic parameter of the living subject. In certain embodiments, the controller may be a microcontroller or a processor. Optionally, in certain embodiments, the controller may be a part of the non-invasive device 110, which is formed integrally with the at least one sensor. Alternatively, in certain embodiments, the controller may be a part of the processing device 120, which is communicatively coupled to but formed separately from the at least one sensor.

In certain embodiments, the system 100 may further include a monitoring device, which is a part of the processing device 120. The monitoring device is configured to communicate with the controller to receive the vascular signals and the at least one hemodynamic parameter, for monitoring condition of the living subject in real time.

In certain embodiments, implementation of the system 100 may vary. For example, the non-invasive device 110 may be in the form of a wearable band, an adhesive, or an attachment being in contact with a surface of skin of the living subject overlying at least one peripheral vein, artery or perfused tissue, such that the sensor may acquire the vascular signals from the at least one peripheral vein, artery or perfused tissue. In certain embodiments, the controller and/or the monitoring device may be formed integrally within the non-invasive device 110, such that the whole system 100 may be in the form of a stand-alone device (e.g., a watch, a wristband with display, etc.), and the monitoring device may display results of the spectral analysis on the stand-alone device without using any additional, separate device. Alternatively, the monitoring device of the processing device 120 may be a smartphone, a tablet computing device, a laptop computing device, a desktop computing device, or any combination thereof, which is formed separately from the non-invasive device 110, such that the results of the spectral analysis may be displayed on the monitoring device. In one embodiment, the monitoring device communicates with the controller of the non-invasive device 110 via a wireless protocol.

Figure 2:
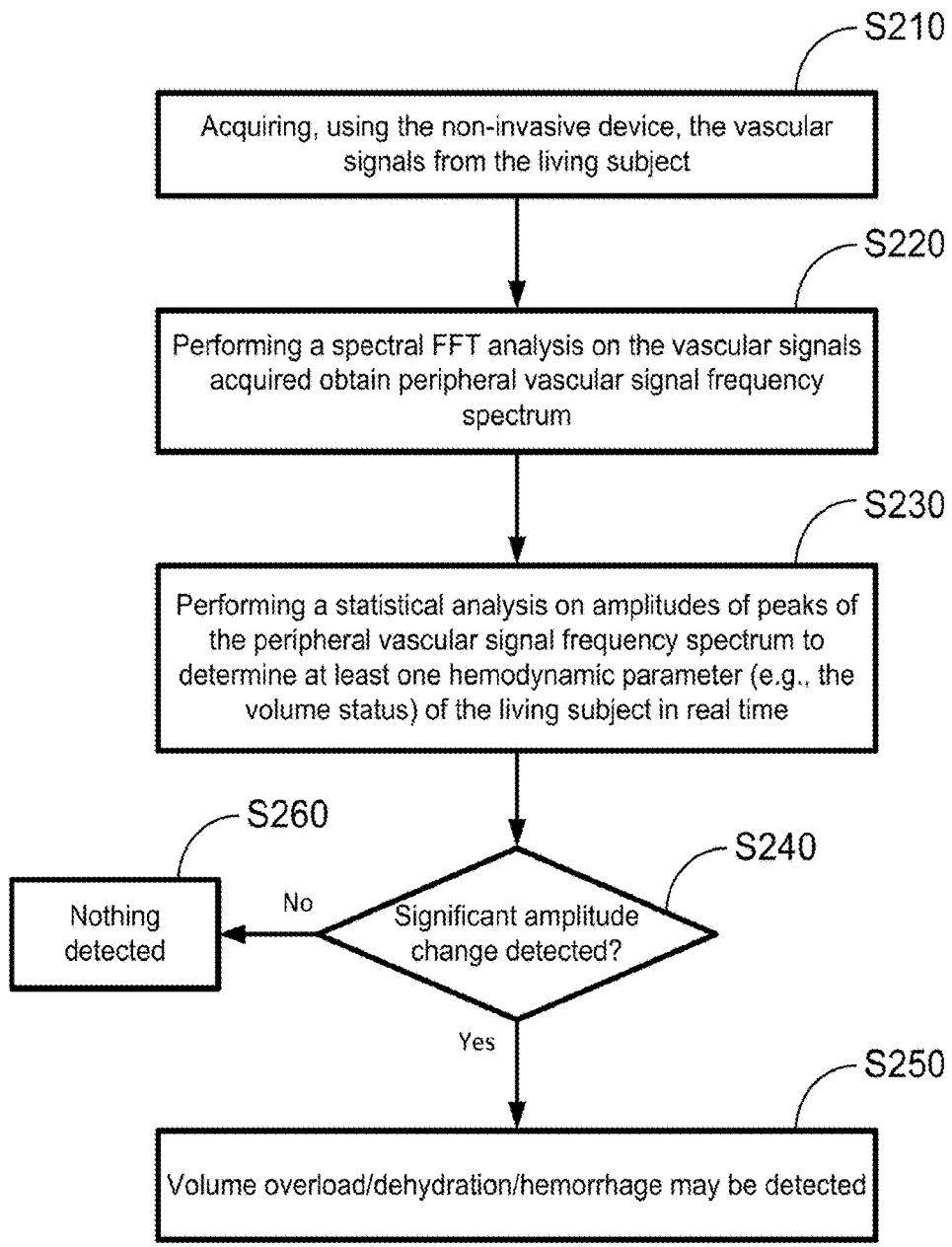
FIG. 2 shows a flowchart of a method for detecting or monitoring intravascular volume status, volume overload, dehydration, hemorrhage, cardiac/renal/hepatic function, pulmonary embolism, vascular endothelial function, vascular compliance, and/or real time assessment of resuscitation of a living subject using the NIVA system according to certain embodiments of the present invention.

FIG. 2 shows a flowchart of a method for detecting or monitoring intravascular volume status, volume overload, dehydration, hemorrhage, cardiac/renal/hepatic function, pulmonary embolism, vascular endothelial function, vascular compliance, and/or real time assessment of resuscitation of a living subject using the NIVA system according to certain embodiments of the present invention. In certain embodiments, the NIVA system as shown in FIG. 1 may be used to perform the method as shown in FIG. 2.

As shown in FIG. 2, at step S210, the non-invasive device 110 is used to acquire the vascular signals from the living subject. Specifically, the non-invasive device 110 may be disposed in contact with a surface of skin of the living subject overlying at least one peripheral vein, artery or perfused tissue, such that the sensor of the non-invasive device 110 may acquire the vascular signals.

At step S220, upon receiving the vascular signals from the non-invasive device 110, the processing device 120 performs a spectral process and analysis, such as a spectral fast Fourier transform (FFT) analysis, on the vascular signal to obtain a peripheral vascular signal frequency spectrum. At step S230, the processing device 120 performs a statistical analysis on amplitudes of peaks of the peripheral vascular signal frequency spectrum to determine at least one hemodynamic parameter of the living subject in real time. In certain embodiments, the at least one hemodynamic parameter of the living subject may include information of volume status, heart rate, heart rate variability, oximetry, blood pressure, pulse pressure variability, temperature, and respiratory rate of the living subject. For example, when the amplitudes of peaks of the peripheral vascular signal frequency spectrum are analyzed to determine the volume status of the living subject, volume overload, dehydration, hemorrhage and/or real time assessment of resuscitation may then be detected based on the volume status of the living subject. For example, at step S240, the processing device 120 determines whether a significant amplitude change of the peaks is detected. If so, at step S250, the processing device 120 determines that the living subject has a volume overload, dehydration, or hemorrhage, such as hypovolemia or hypervolemia, depending on the amplitude change. If not, at step S260, the processing device 120 determines that nothing is detected for the living subject.

Specifically, the steps S210 and S220 may be performed continuously, such that at two different time period, two sets of the peripheral vascular signal frequency spectrums may be obtained by the NIVA system 100. For example, for a time period from $T_0$ to $T_2$, the time period may be divided into a first time period from $T_0$ to $T_1$, and a second time period from $T_1$ to $T_2$, and each of the first time period and the second time period may be used to obtain a separate set of peripheral vascular signal frequency spectrums. In certain embodiments, the time period may be divided into more than two time periods, and multiple sets of peripheral vascular signal frequency spectrums may be obtained. In certain embodiments, the peripheral vascular signal frequency spectrum obtained at an earlier time period (e.g., the first time period) may be used as a baseline peripheral vascular signal frequency spectrum. Thus, the statistical analysis at step S230 may be performed by obtaining a plurality of baseline peaks $\{B_{N-1}\}$ from a lower frequency side on a baseline peripheral vascular signal frequency spectrum, where N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$. In other words, the baseline peaks may include a first baseline peak $B_0$ corresponding to a first frequency $F_0$, a second baseline peak $B_1$ corresponding to a second frequency $F_1$, a third baseline peak $B_2$ corresponding to a third frequency $F_2$, a fourth baseline peak $B_3$ corresponding to a fourth frequency $F_3, \ldots$, in which each of the frequency $F_N$ is greater than the previous frequency $F_{N-1}$. Then, a plurality of peaks $\{P_{N-1}\}$ may be obtained on the peripheral vascular signal frequency spectrum currently obtained, where the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$. For example, the peaks may include a first peak $P_0$ corresponding to the first frequency $F_0$, a second peak $P_1$ corresponding to the second frequency $F_1$, a third peak $P_2$ corresponding to the third frequency $F_2$, a fourth peak $P_3$ corresponding to the fourth frequency $F_3$. . . . In certain embodiments, the number of peaks on the peripheral vascular signal frequency spectrum equals to the number of baseline peaks on the baseline peripheral vascular signal frequency spectrum. In this way, the volume status or any other hemodynamic parameter of the living subject may be determined in real time by comparing the amplitudes of the peaks to that of the corresponding baseline peaks, respectively.

In certain embodiments, the volume status of the living subject at the second time period indicates hypovolemia or hypervolemia when amplitude changes greater than a threshold are detected from the baseline peaks $\{B_{N-1}\}$ to the peaks $\{P_{N-1}\}$.

In certain embodiments, the plurality of peaks $\{P_{N-1}\}$ includes a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$. Specifically, the first peak $P_0$ corresponding to the first frequency $F_0$ is associated with a respiratory rate of the living subject; the second peak $P_1$ corresponding to the second frequency $F_1$ is associated with a heart rate of the living subject; and the third peak $P_2$ corresponding to the third frequency $F_2$ and the fourth peak $P_3$ corresponding to the fourth frequency $F_3$ are associated with harmonics of the living subject.

Various types of sensors may be used as the sensor of the non-invasive device 110. In certain embodiments, the sensor of the non-invasive device may include a piezoelectric sensor, a resistive pressure/force sensor, an optical wavelength selective reflectance or absorbance measurement system, a tonometer, an ultrasound, bioimpedance, plethysmography, or pressure transducer, or any combination thereof.

Figure 3A:
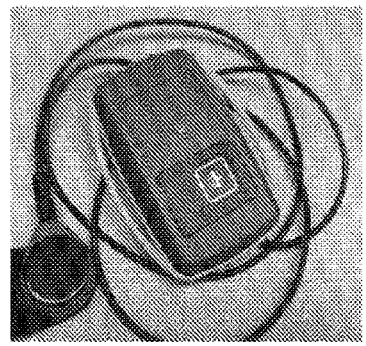
FIG. 3A shows a non-invasive device including a microcontroller and a piezoelectric sensor according to certain embodiments of the present invention.

FIG. 3A shows a non-invasive device including a microcontroller and a piezoelectric sensor according to certain embodiments of the present invention. Specifically, as shown in FIG. 3A, the non-invasive device 300 is formed integrally by the microcontroller and the piezoelectric sensor as a single device, without the need of a separate monitoring device. The sensor being used in the non-invasive device 300 is a piezoelectric sensor.

In certain embodiments, the non-invasive piezosensor data being obtained by the piezoelectric sensor may be transmitted in real time to LabChart software on a laptop computer through PowerLab acquisition software. This table-top system can be used immediately for clinical tests. In addition to the piezoelectric sensors, all patients had state-of-the-art non-invasive and invasive hemodynamic monitors for comparison.

Figure 3B:
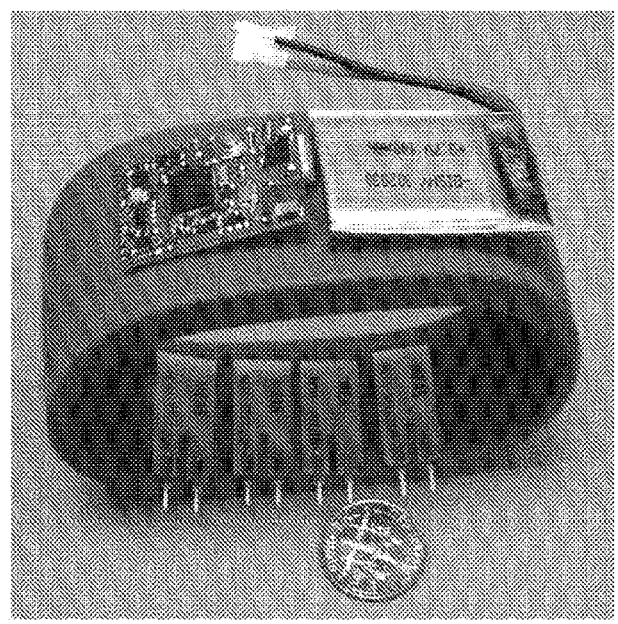
FIG. 3B shows a non-invasive device in the form of a wristband according to certain embodiments of the present invention.

FIG. 3B shows a non-invasive device in the form of a wristband according to certain embodiments of the present invention. As shown in FIG. 3B, the non-invasive device 300' is implemented in the form of a wearable device, such as the wristband, which has a microcontroller, a battery, and an array of piezoelectric sensors. FIG. 3C shows Bluetooth communication from a wristband to a smartphone application to determine volume status according to certain embodiments of the present invention. Specifically, as shown in FIG. 3C, the non-invasive device 300' is implemented in the form of a wearable device, such as the wristband as shown in FIG. 3B, and a smartphone 320 is provided as the monitoring device of the system. The alert mechanism may be provided on the wearable device itself and/or on the smartphone application. The mobile application is displaying various hemodynamic variables, including heart rate, volume status (current and trends), temperature, and respiratory rate. Specifically, off-the-shelf miniature thin film based piezoelectric sensors are evaluated in order to determine the sensor with the optimal signal and sensitivity, which can be incorporated into the wearable wristband configuration of the invention. The different sensor configurations can be tested with the wristband using a standard PowerLab/LabChart data acquisition system. It is envisioned to integrate miniature piezoelectric sensor arrays interfaced with a miniature microcontroller board with Bluetooth capabilities into a wearable wristband, which is battery operated.

In certain embodiments, the wearable device may include a display device or a display mechanism which visualizes the output of the processing device (i.e., the controller and/or the monitoring device). For example, the display device or mechanism may be a color indicator, which includes multiple fields of different colors to show the output. Alternatively, the display device or mechanism may be a number, a fuel gauge, a moving bar, or any other device or mechanism suitable to display the output (e.g., the physiological data of the living subject). In certain embodiments, the monitoring device may display the output in a similar fashion in combination with the physiological variables obtained from the vascular bed.

In certain embodiments, the wearable device could be streaming data to a phone or computer over Bluetooth, with non-invasive peripheral vascular waveform analysis including, but not limited to Fourier transform analysis and algorithm implementation to compute the volume status on the smart phone/computer. The implementation of a real time signal processing on the smart phone is straightforward and leads to a portable, wireless, wristband based device that can determine the intravascular volume status in real-time. Eventually the volume status or any other physiological variables can be computed on the microcontroller, which could display the status on the wristband or communicates any changes in condition to the paired smart phone via Bluetooth to conserve battery power.

Figure 4A:
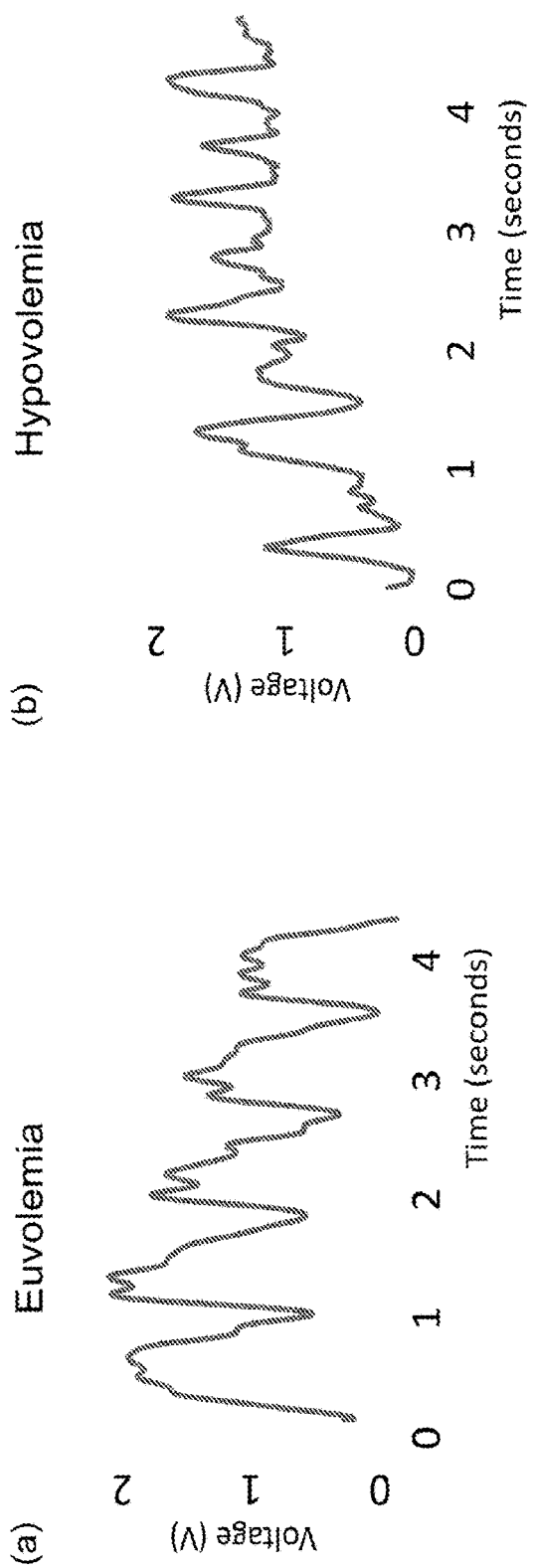
FIG. 4A shows charts of piezoelectric transducer recordings of vascular signals from a patient wrist in states of (a) euvolemia and (b) hypovolemia, according to certain embodiments of the present invention.
Figure 4B:
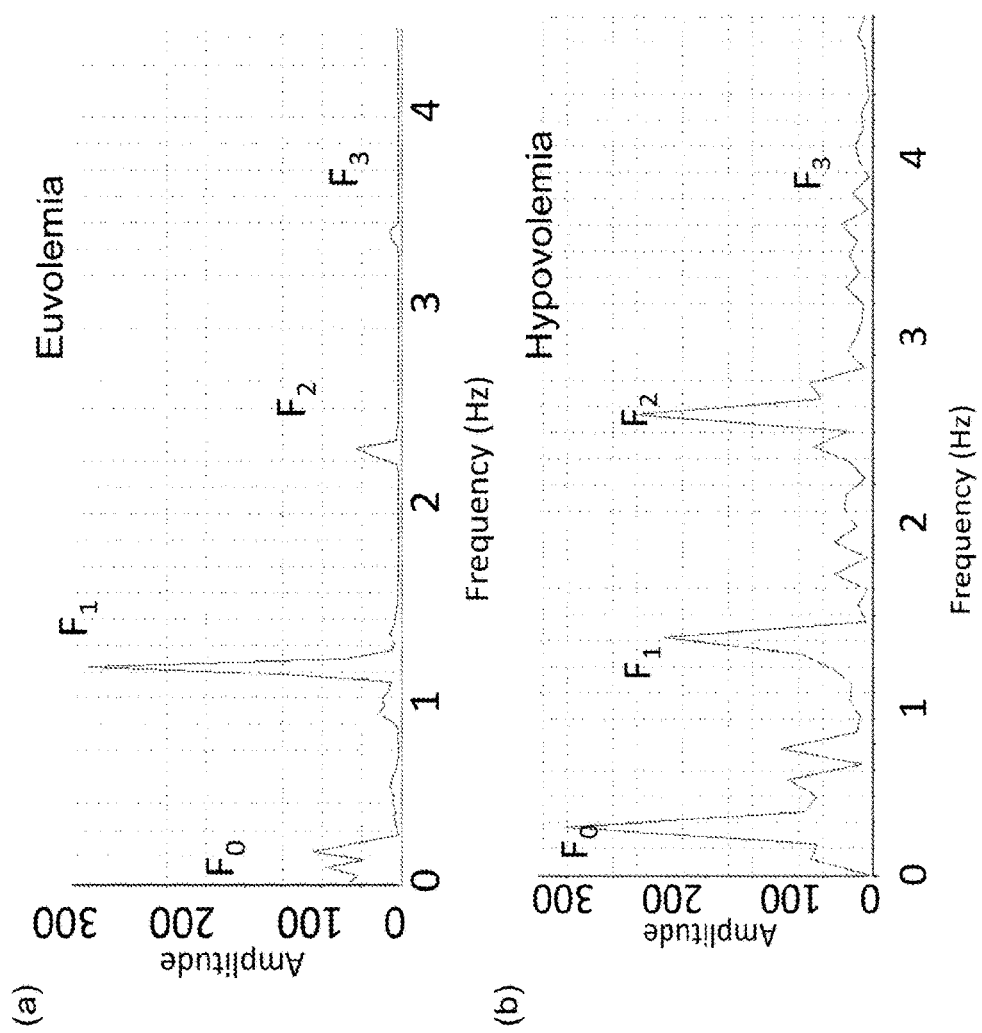
FIG. 4B shows peripheral vascular signal frequency spectrums obtained from the vascular signals as shown in FIG. 4A, according to certain embodiments of the present invention.

It has been found that piezoelectric sensors provide an excellent real-time peripheral vascular pulse waveform signal. FIG. 4A shows charts of piezoelectric transducer recordings of vascular signals from a patient wrist in states of (a) euvolemia and (b) hypovolemia, according to certain embodiments of the present invention, and FIG. 4B shows peripheral vascular signal frequency spectrums obtained from the vascular signals as shown in FIG. 4A, according to certain embodiments of the present invention. Specifically, the peripheral vascular signal frequency spectrums as shown in FIG. 4B are obtained by performing Fourier transformation of the vascular signals as shown in FIG. 4A. The preliminary hypovolemia data as shown in FIGS. 4A and 4B is based on the use of non-invasive piezoelectric sensors placed directly on the skin of cardiac surgery patients undergoing planned autologous blood donation or during exercise. The sensors were interfaced with LabChart (ADInstruments) for data acquisition and analysis. Signals were measured in real time before and during autologous blood donation of up to 10% of blood volume. Then, a spectral decomposition is performed using Fourier transformation techniques.

As shown in FIG. 4B, in each of the peripheral vascular signal frequency spectrums, a plurality of peaks may be observed, and each of the peaks may correspond to a plurality of frequencies $F_0$, $F_1$, $F_2$ and $F_3$. Specifically, the first peak $P_0$ corresponding to the first frequency $F_0$ is associated with a respiratory rate of the living subject, the second peak $P_1$ corresponding to the second frequency $F_1$ is associated with a heart rate of the living subject; and the third peak $P_2$ corresponding to the third frequency $F_2$ and the fourth peak $P_3$ corresponding to the fourth frequency $F_3$ are associated with harmonics of the living subject.

It should be noted that, although piezoelectric sensors may be used as the sensor of the non-invasive device, other pressure/force sensitive transducer such as force sensitive resistors could be used for this purpose. In certain embodiments, the sensor being used may include a piezoelectric sensor, a resistive pressure/force sensor, an optical wavelength selective reflectance or absorbance measurement system, a tonometer, an ultrasound, bioimpedance, plethysmography, or pressure transducer, or any combination thereof.

In certain embodiments, the system, method and NIVA device may be used for detections of hemorrhage earlier than standard and invasive vital sign monitoring: The inventors have done extensively studies in hemodynamic monitoring and spectral analysis of physiologic signals such as heart rate, impedance, respiration, and blood pressure. The initial trails in human patients show that peripheral vascular analysis measured with non-invasive piezoelectric transducers can be used as a sensitive, real-time monitor for hemorrhage.

Figure 5A:
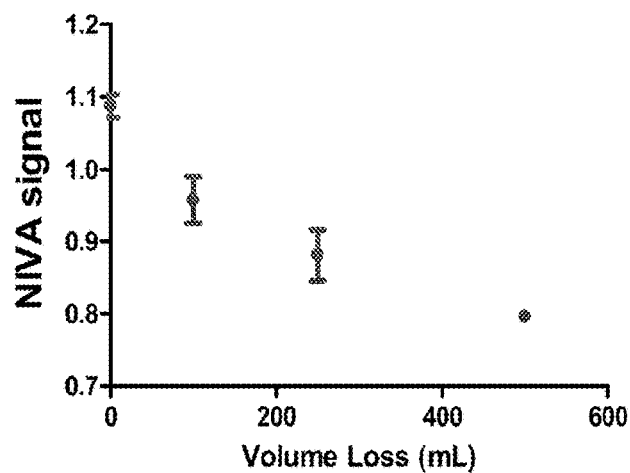
FIG. 5A shows a chart of the $F_1$ amplitude of the NIVA signals for detecting hemorrhage in the human model for volume status according to certain embodiments of the present invention.
Figure 5B:
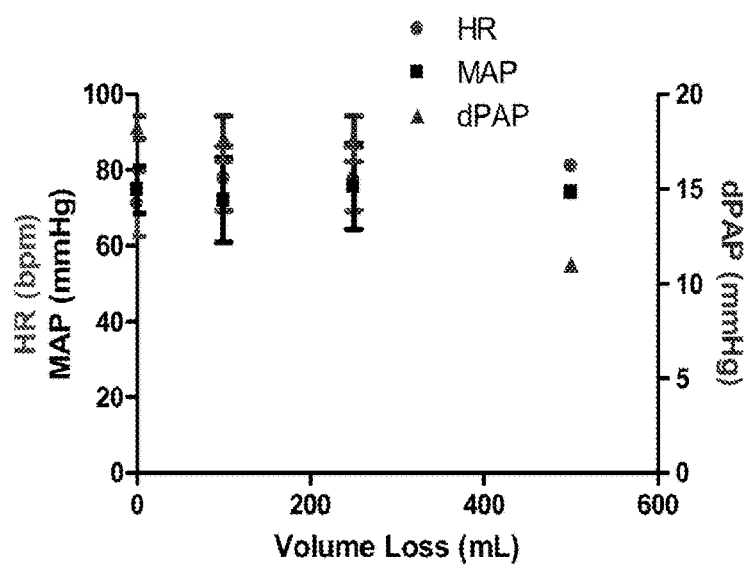
FIG. 5B shows a chart of mean arterial pressure (MAP), heart rate (HR), and diastolic pulmonary artery pressure (dPAP) for detecting hemorrhage in the human model for volume status according to certain embodiments of the present invention.

FIG. 5A shows a chart of the $F_1$ amplitude of the NIVA signals for detecting hemorrhage in the human model for volume status according to certain embodiments of the present invention. In comparison, FIG. 5B shows a chart of mean arterial pressure (MAP), heart rate (HR), and diastolic pulmonary artery pressure (dPAP) for detecting hemorrhage in the human model for volume status according to certain embodiments of the present invention. Specifically, FIGS. 5A and 5B demonstrate that the device detects early onset hemorrhage in humans (n=3). As shown in FIG. 5B, there were no changes in blood pressure, heart rate, or invasive pulmonary artery pressure until significant (>10%) of blood loss had occurred. Further, it has been discovered that the peripheral non-invasive device is independent of intrathoracic changes during mechanical ventilation—a substantial advancement for non-invasive monitoring of both spontaneously breathing and mechanically ventilated patients.

Figure 6:
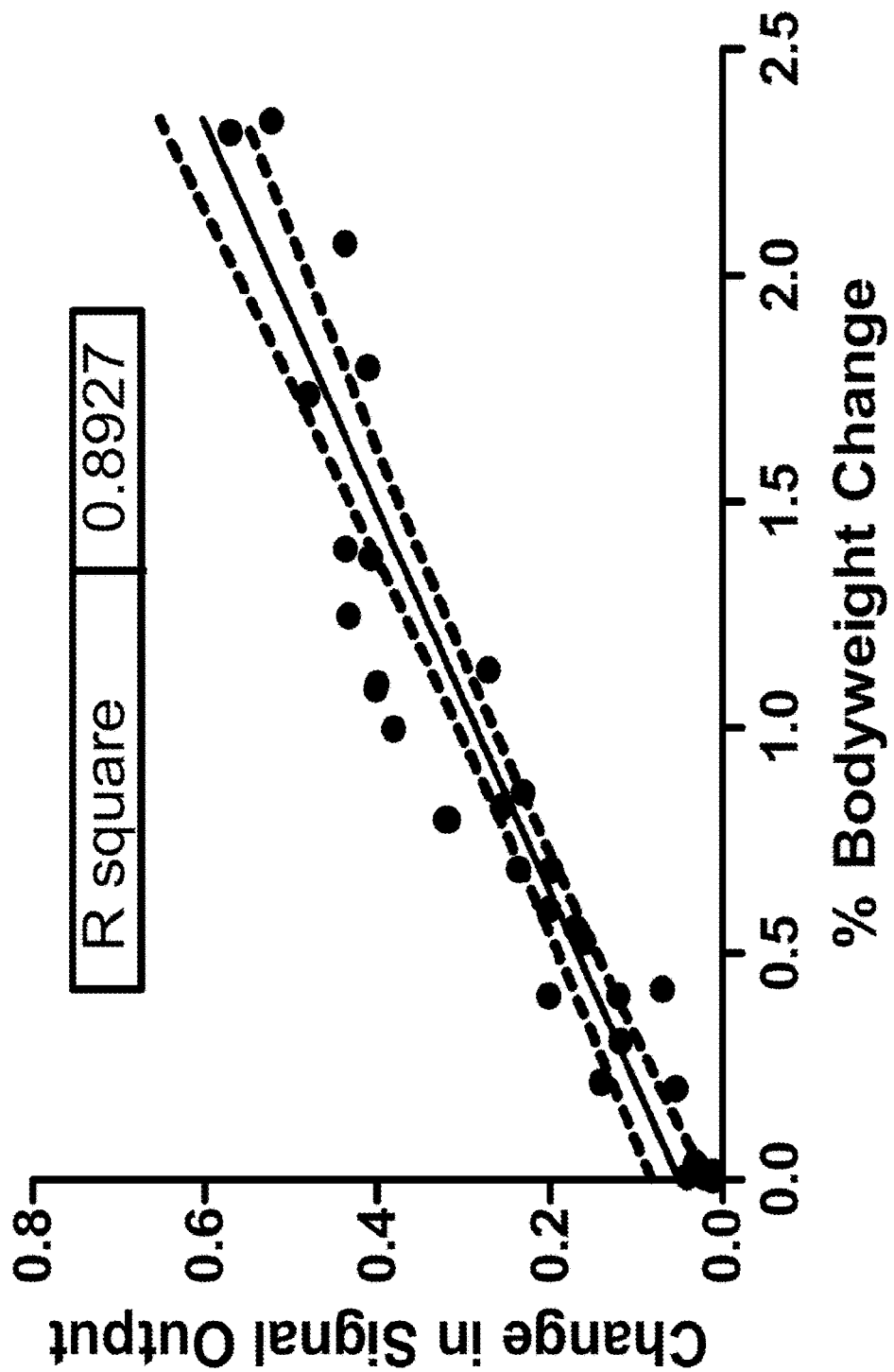
FIG. 6 shows non-invasive vascular analysis for detecting dehydration following strenuous exercise ($p<0.001$, $n=33$), according to certain embodiments of the present invention.

In certain embodiments, the system, method and NIVA device may be used for detections of dehydration. FIG. 6 shows non-invasive vascular analysis for detecting dehydration following strenuous exercise (p<0.001, n=33), according to certain embodiments of the present invention. Specifically, as shown in FIG. 6, detection of hydration status following exercise is demonstrated with spectral analysis output compared to % body weight change before and after exercise.

Based on the studies, the system, method and NIVA device may be used to detect dehydration from water and salt loss during intense heat and exercise, as shown in FIG. 6. These studies validate the ability for the NIVA to detect intravascular volume depletion in men and women of various age and body mass indices. A promising extension of this technology is dehydration detection and effectiveness of oral rehydration therapy. This technology would be useful to guide oral rehydration therapy for optimal physical performance in extreme heat, humid, and dry environmental conditions. Another life-saving application is early hypovolemia detection in patients with diarrheal disease, particularly in global settings.

Figure 7:
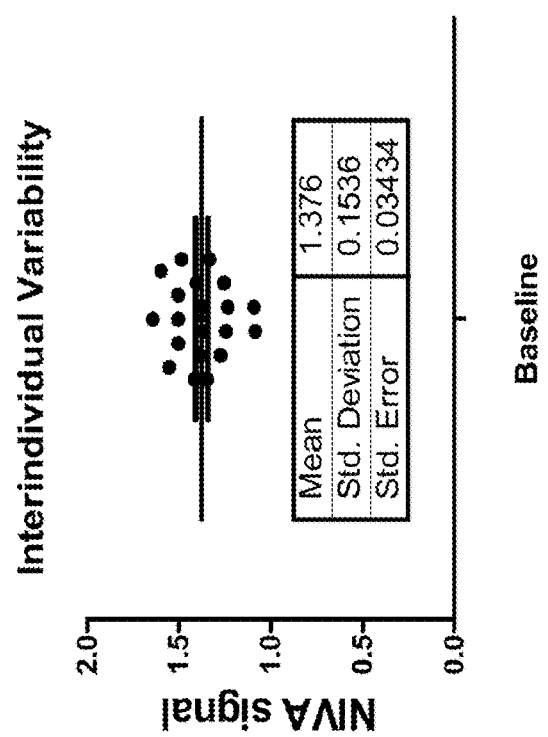
FIG. 7 shows a chart of interindividual variability of NIVA signal at baseline for 25 people according to certain embodiments of the present invention.

In certain embodiments, the system, method and NIVA device may be used for detection of fluid overload in humans. Specifically, the unique signals of volume overload using non-invasive vascular analysis have been demonstrated in patients (n=25) with congestive heart failure. The inventors have studied patients throughout their hospitalization for congestive heart failure from a state of volume overload through the diuresis and treatment period until restoration of a baseline volume and physiologic state. FIG. 7 shows a chart of interindividual variability of NIVA signal at baseline for 25 people according to certain embodiments of the present invention. As shown in FIG. 7, the mean value was 1.376 with a standard error of the mean of 0.03434. These methods may be useful for managing a wide range of patients with volume overload including, but not limited to, patients with heart and renal failure. The non-invasive methods may be used in the outpatient or inpatient settings with alerts and data sent to the patient and care provider for proactive measures. In certain embodiments, the alerts/trends for outpatient or inpatient hospital monitoring patients may be in connection with the following symptoms: heart failure, renal failure/dialysis, dehydration, etc. Analysis of real-time and historical trends can be used to prevent hospitalization of patients for volume overload.

Certain embodiments of the present invention may relate to a miniaturized, wireless, networked wearable device of a piezoelectric transducer recording system. The system is corresponding to a wireless non-invasive monitor for volume status determination. In one embodiment, low cost, off-the-shelf components are utilized for a smart wristband based device with a smartphone application to determine real-time intravascular volume status, which offers a substantial advantage over current methods for the detection of dehydration, hemorrhage and guided resuscitation.

In certain embodiments, an innovative point-of-care wristband based device and corresponding mobile applications may be provided to detect hemorrhage and guide fluid resuscitation, useable in the combat or trauma casualty setting. This aspect of the invention includes, but is not limited to, fabrication of a non-invasive wristband based POC device for hemorrhage detection and staging; mobile applications with user-friendly interface; and algorithm-based decision support for hemorrhage. In certain embodiments, the mobile application may control the device to display intravascular volume analysis in real-time and historical trends, and to send alerts for hypovolemia, euvolemia, and hypervolemia during evaluation and resuscitation. In certain embodiments, the alerts/trends for outpatient or inpatient hospital monitoring patients may be in connection with the following symptoms: heart failure, renal failure/dialysis, dehydration, etc. In certain embodiments, the mobile application may communicate with a remote server or other mobile devices for storage and data transmission or communication with care providers.

In the following examples, the inventors have utilized NIVA in different models, including a porcine hemorrhage model and a controlled human model. The preliminary results obtained with the tabletop data acquisition system in a porcine hemorrhage model and from measurements during autologous blood donation demonstrate the feasibility of a non-invasive low cost wearable wristband point of care device to determine the fluid status in humans. The tests in the examples are performed in standardized settings in order to test the hypothesis that NIVA is far more sensitive and specific than standard and invasive vital sign monitoring.

EXAMPLE 1

In one example, a wearable device, including but not limited to a wristband-based device as shown in FIG. 3B, is provided to replace the tabletop system. The example focuses on optimizing the piezoelectric transducer and evaluate a miniature piezoelectric thin film/foil based transducer system (LDT0-028K-Measurement Specialties, Inc., Hampton, Va.). Specifically, the LDT0-028K is a flexible component comprising a 28 µm thick piezoelectric PVDF polymer film with screen-printed Ag-ink electrodes, laminated to a 0.125 mm polyester substrate, and fitted with two crimped contacts. As the piezo film is subjected to motion it is displaced from the mechanical neutral axis, bending creates very high strain within the piezopolymer and therefore high voltages are generated. The voltage generated can be directly interfaced using a resistor network to an analog digital converter of either the tabletop data acquisition system or a standalone microcontroller system. In one embodiment, an array of piezoelectric transducers may be fitted onto the lower circumvent of the wristband to evaluate the ideal most robust sensor position and configuration to obtain optimum pulse pressure wave forms. Performance criteria are the signal to noise ratio and the sensitivity to detecting the volume status in patients. With the flexible high gain piezo transducer array, the signal to noise ratio is increased and the error resulting from sensor placement is eliminated. Preliminary measurements using the LDT0-028K sensor show a larger voltage output and an identical waveform than our current sensor configuration. However, any pressure/force sensitive transducer can be used for this purpose.

Once the ideal sensor and sensor configuration is determined, the piezo transducers are interfaced with a miniature microcontroller board with integrated Bluetooth capabilities from Panasonic (PAN1721). The PAN1721 is a cost-effective, ultralow-power, system-on-chip (SoC) for Bluetooth Low Energy applications. The module includes an eight channel 12-bit analog-to-digital converter, 19 GPIOs plus battery and temperature sensors. The PAN1721 combines an excellent RF transceiver with a high performance low power 8051 microcontroller, in-system programmable flash memory, 8-kB RAM, and many other powerful supporting features. The inventors (in the Baudenbacher lab) have used software compatible Bluetooth modules from Panasonic and has acquired all the firmware to implement the Bluetooth stack on both Android or Apple based Smart Phones. The Panasonic module transmits pulse waveforms to the smart phone in real time. In one embodiment, the smart phone performs the mathematical analysis, compute the volume status and display the information graphically. In one embodiment, a deployable device is equipped with a microcontroller platform capable to perform the mathematical analysis of the waveform in real time, display the results on the wristband and alert the phone if a critical status occurs or if queried to reduce the amount of data transmitted.

Algorithm-based decision support is accomplished by determining the rate and severity of hemorrhage along with potential other physiological variables. The smartphone application displays in real-time intravascular volume analysis and sends alerts for hypovolemia and euvolemia during resuscitation or dehydration, as shown in FIG. 3C. Continuous automated monitoring and feedback for the field medic or care provider allows guided goal-directed fluid resuscitation, currently not possible in the field, for optimal end organ perfusion, and improved survival. The device data can be seamlessly integrated into existing cloud based data servers and mobile applications for remote monitoring, emergency medical decision support and record keeping. Centralized data collection and analysis aid in prioritizing care and triage of multiple casualties. The capabilities of the POC device could be expanded to include multiple sensor modalities for example heart rate, heart rate variability, cardiac output, blood pressure, body temperature, respiratory rate, hydration or lactate beside volume status to provide a more complete health monitor device in the field.

In one embodiment, the sensitivity of the wearable wristband based device for detecting hemorrhage and quantitating hemorrhage in pigs is determined. Early, compensated hemorrhagic shock is difficult to detect with standard vital sign monitoring. The preliminary data shows that our device provides a sensitive method for detecting hypovolemia. In one embodiment, a wireless device is used to determine thresholds for euvolemia and hypovolemia.

To demonstrate proof of concept, adult Yorkshire Landrace Hybrid pigs weighing 40-50 kg is anesthetized, intubated, and mechanically ventilated. In addition to standard vital sign monitors, invasive catheters are used for arterial pressure and pulmonary artery pressure measurements. A transthoracic echocardiogram probe is placed for visualizing cardiac structures and chamber size in real-time. The device is placed on the upper extremity of the pig. Standard invasively obtained hemodynamic measurements and device output are continuously obtained and displayed on LabChart software. Successive, graded exsanguination at a rate of 50 mL/min is performed for determining the sensitivity of hemorrhage detection in a porcine animal model. Exsanguination is terminated with a 10% decrease in systolic blood pressure, hemodynamic instability, or clinical evidence of shock. Following exsanguination, the total volume of autologous blood is incrementally transfused back to the pigs at a rate of 50 mL/min to determine effects of resuscitation with our device. Among other things, the following parameters are monitored throughout the protocol:

Venous Wave Form Analysis
Standard vital sign monitoring: heart rate, electrocardiogram, and pulse oximetry (blood pressure is directly measured via an intra-arterial catheter).
Central venous pressure.
Intra-arterial blood pressure.
Cardiac Output/Index.
Pulmonary artery pressure.
Transthoracic Echocardiogram: left ventricular systolic function and end-diastolic area; right ventricular function and basal/mid chamber diameter.

In certain embodiments, the venous waveform analysis may be compared with estimated blood loss, volume/type of fluid resuscitation, serum lactate, and hemoglobin levels throughout the protocol. These studies allow us to define specific parameters that correspond to actual volume changes. Thus, instead of relative units of change determined by the device, there are absolute values that correspond with specific changes in volume status.

With a difference of means between hemorrhage and euvolemia through our algorithm was 0.23 A.U. with a standard deviation of 0.27 using a type I error probability associated with the test of 0.05, and a power of 0.95 we were able to determine that 20 pigs would give a sufficient sample size for experimentation. It is assumed that X and Y values are samples that follow a Gaussian distribution. Standard (Pearson) correlation is used to compare Fourier frequency amplitudes and frequency ratios, to invasive monitoring parameters. All X and Y values are measured independently. Both positive and negative correlations are measured with statistical significance defined as $p<0.05$. Next, the coefficient of determination, r2, determines the fraction of variance shared by the measured parameters. In the presence of a linear correlation, multiple regression analysis is performed using statistical software and intradepartmental statistical consultation.

An extension of this protocol is the ability to detect intravascular volume overload due to excessive fluid administration. Hypervolemia studies are performed by administering 50 ml/kg of balanced crystalloid solution to euvolemic pigs while continuously monitoring, physiologic parameters, transesophageal echocardiography, and clinical findings. After each liter of crystalloid infused, a hemoglobin level is obtained in order to consider the effects of hemodilution on venous waveform analysis. In one embodiment, the Fourier transformation is used to decompose vascular waveforms and correlate the frequency amplitudes with total volume removed for deriving a robust algorithm for hemorrhage detection and resuscitation used for subsequent human studies.

EXAMPLE 2

In certain embodiments, the device using non-invasive vascular waveform analysis for hemorrhage detection and staging in humans is validated. In compliance with the Institutional Review Board, the inventors planned to enroll 50 patients who present for coronary artery bypass surgery who have normal ventricular and valve function. It is standard practice for patients to undergo preoperative autologous blood donation in order to conserve clotting factors, often consumed during cardiopulmonary bypass. Cardiac surgery also offers an opportunity to compare real time changes in hemodynamic parameters with our device parameters in a challenging heterogeneous group of patients.

Prior to the start of surgery, the patients are induced with general anesthesia and mechanically ventilated. Invasive monitors are inserted as per standard anesthesia protocol to include central venous, pulmonary artery, and intra-arterial catheterization. A transesophageal echocardiogram is routine practice and used for this study to measure ventricular chamber size and function. The device is attached to the patient's wrist for beat-to-beat recording of peripheral vascular waveforms. The above disclosed algorithm is used for detecting and staging hemorrhage. Prior to the start of surgery, up to 10 mL/kg autologous blood donation occurs over a 15-minute period. Blood removal is terminated at 10 mL/kg blood loss or presence of a 10% decrease in baseline systolic blood pressure. The algorithm-based device output is compared to the following parameters which represent the current standard of care for volume determination and resuscitation guidance during cardiac surgery:

Standard vital sign monitoring: heart rate, electrocardiogram, non-invasive blood pressure, and pulse oximetry.
Central venous pressure
Pulmonary artery pressure
Invasive intra-arterial blood pressure
Cardiac output/Stroke volume
Tranesophageal echocardiography: left ventricular end-diastolic area and right ventricular basal/mid diameter.

In addition, the device output is compared with estimated blood loss, volume/type of fluid resuscitation, serum lactate, and hemoglobin levels throughout the cardiac procedure. Standard cardiac surgery provides a unique opportunity to monitor acute changes in volume status and cardiovascular hemodynamics in real time under controlled conditions. Using univariate and multivariate analysis, the inventors are capable of determining how the results from the device correlate with actual volume loss. The device is compared to all other signals to ensure that we are able to make a more accurate estimation of hemodynamic stability. This strategy allows us to define absolute values for the device to detect intravascular volume status and various stages of hemorrhage in humans. It also allows optimization of our device if deficiencies are identified during testing. No patient follow-up beyond the acute resuscitative efforts is performed. Private health information remains de-identified. De-identified data are stored indefinitely on a password-protected computer.

There were selected patients undergoing coronary artery bypass procedures. While this is patient population itself is not representative of young people, this approach gives the inventors a controlled hemorrhage model in a population with real-time invasive hemodynamic and echocardiographic monitoring. Patients were selected with normal ventricular and valve function, representative of young people. Further, as patients were enrolled with diverse demographics, there may be differences in signal output and thresholds for detecting hemorrhage. The inventors did not expect this to be the case as the preliminary data in a human dehydration model detected intravascular volume loss following intense exercise in both men and women across a wide range of body mass index, and age. There are ethical limitations for inducing volume overload in humans.

With a difference of means between hemorrhage and euvolemia in a heterogeneous human population through our algorithm of 0.23 A.U. and a standard deviation of 0.37 and using a type I error probability associated with the test of 0.01, and a power of 0.95 we were able to determine that 50 patients would give a sufficient sample size for experimentation.

Figure 8:
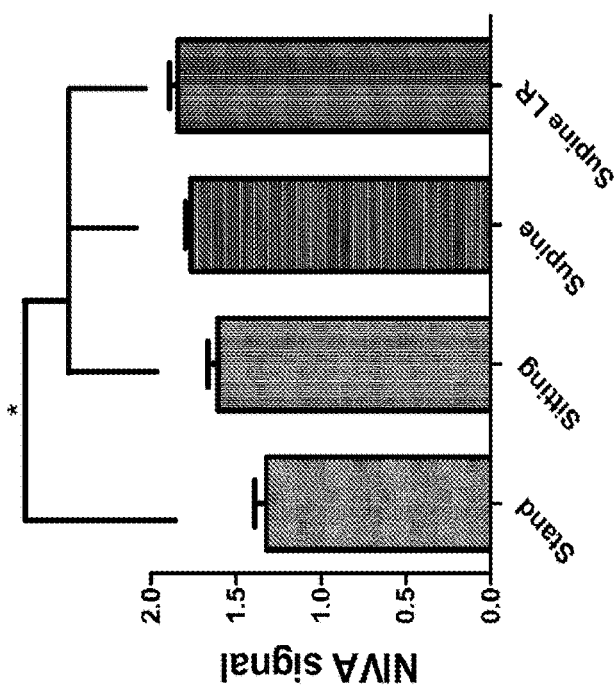
FIG. 8 shows a chart and a corresponding table of how NIVA signals vary due to postoral changes in a patient according to certain embodiments of the present invention.

FIG. 8 shows a chart and a corresponding table of how NIVA signals vary due to postoral changes in a patient according to certain embodiments of the present invention. As shown in FIG. 8, patients when standing have a significantly lower NIVA signal than when sitting, supine or supine with legs raised (LR). The NIVA signal when sitting is lower than it is when supine or supine with legs raised.

Figure 9:
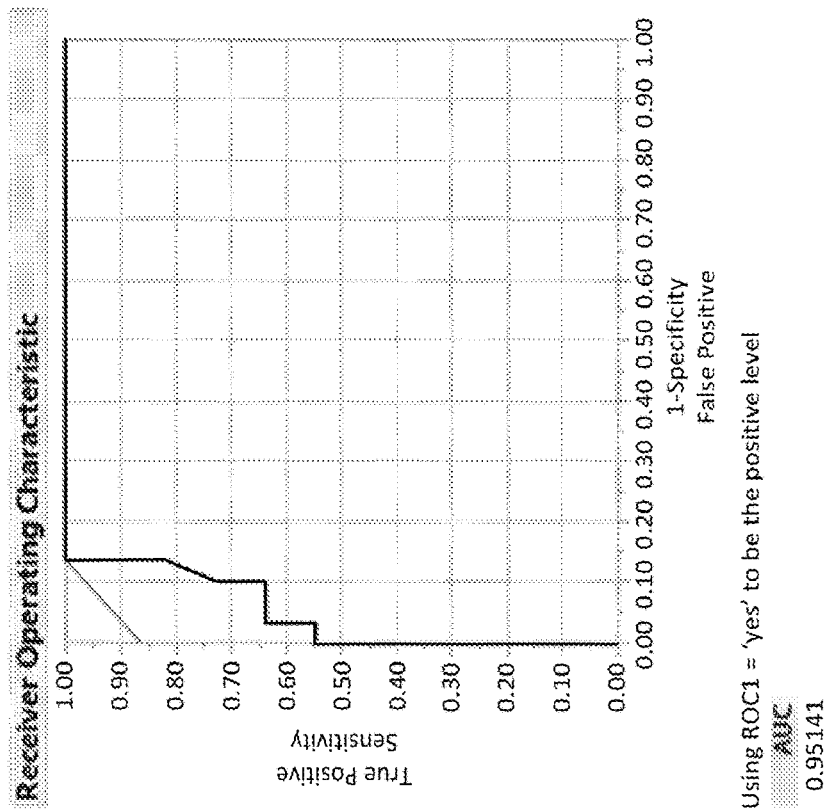
FIG. 9 shows a chart of the receiver operating characteristics according to certain embodiments of the present invention.

FIG. 9 shows a chart of the receiver operating characteristics according to certain embodiments of the present invention, which shows how NIVA can be used to detect dehydration. Specifically, using 26 patients' hydration status NIVA signals are used for the data as shown in FIG. 9 in order to detect presence of 1% dehydration with an area under the curve (AUC) of 0.95.

Figure 10:
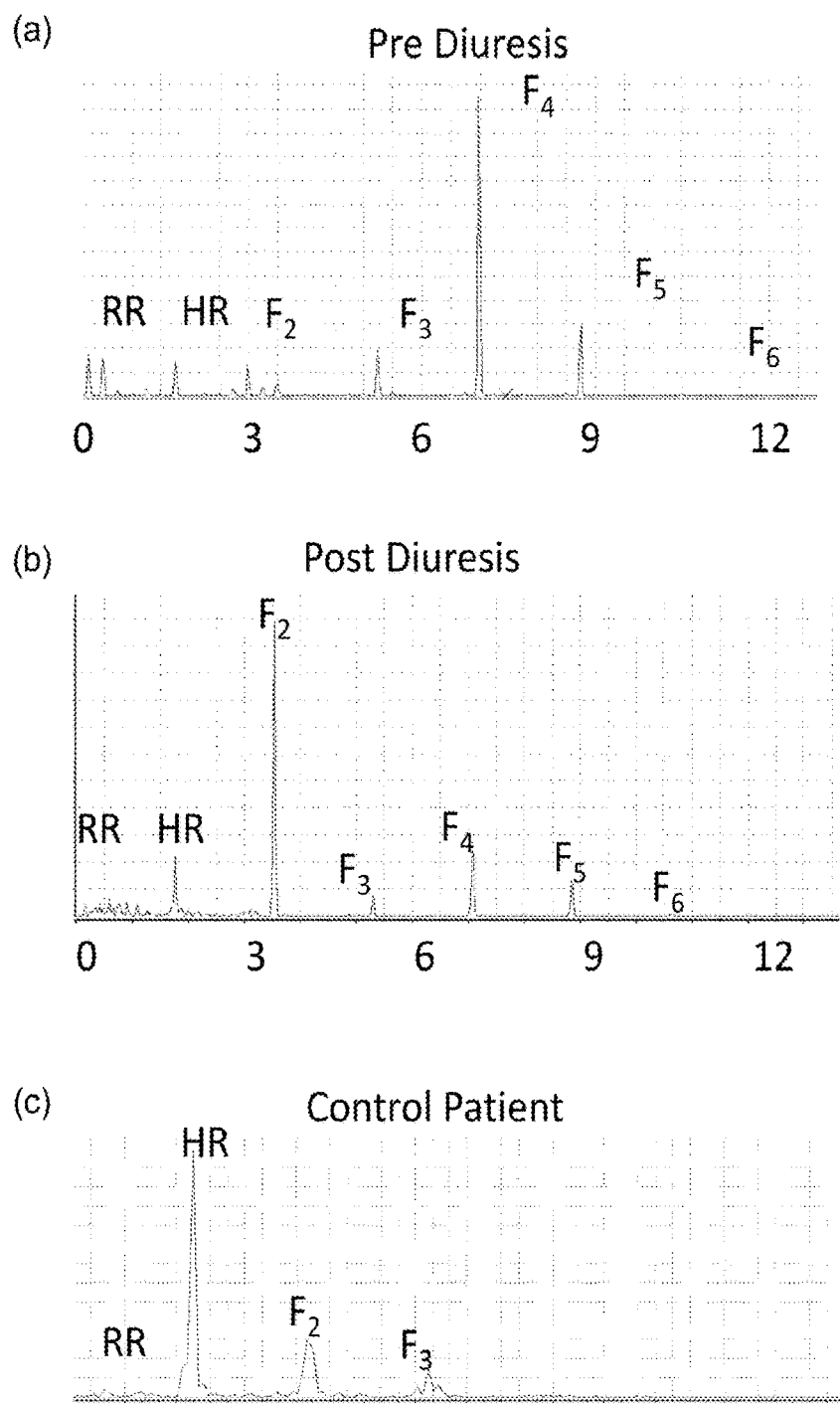
FIG. 10 shows charts of a patient's NIVA signal of (a) pre-diuresis and (b) post-diuresis, and (c) the NIVA signal of a control patient according to certain embodiments of the present invention.

FIG. 10 shows charts of a patient's NIVA signal of (a) pre-diuresis and (b) post-diuresis, and (c) the NIVA signal of a control patient according to certain embodiments of the present invention. Specifically, FIG. 10 shows how the NIVA signal would look before diuresis, after diuresis and in comparison to a control patient, thus demonstrating how NIVA can be used to detect volume overload in patients.

Figure 11:
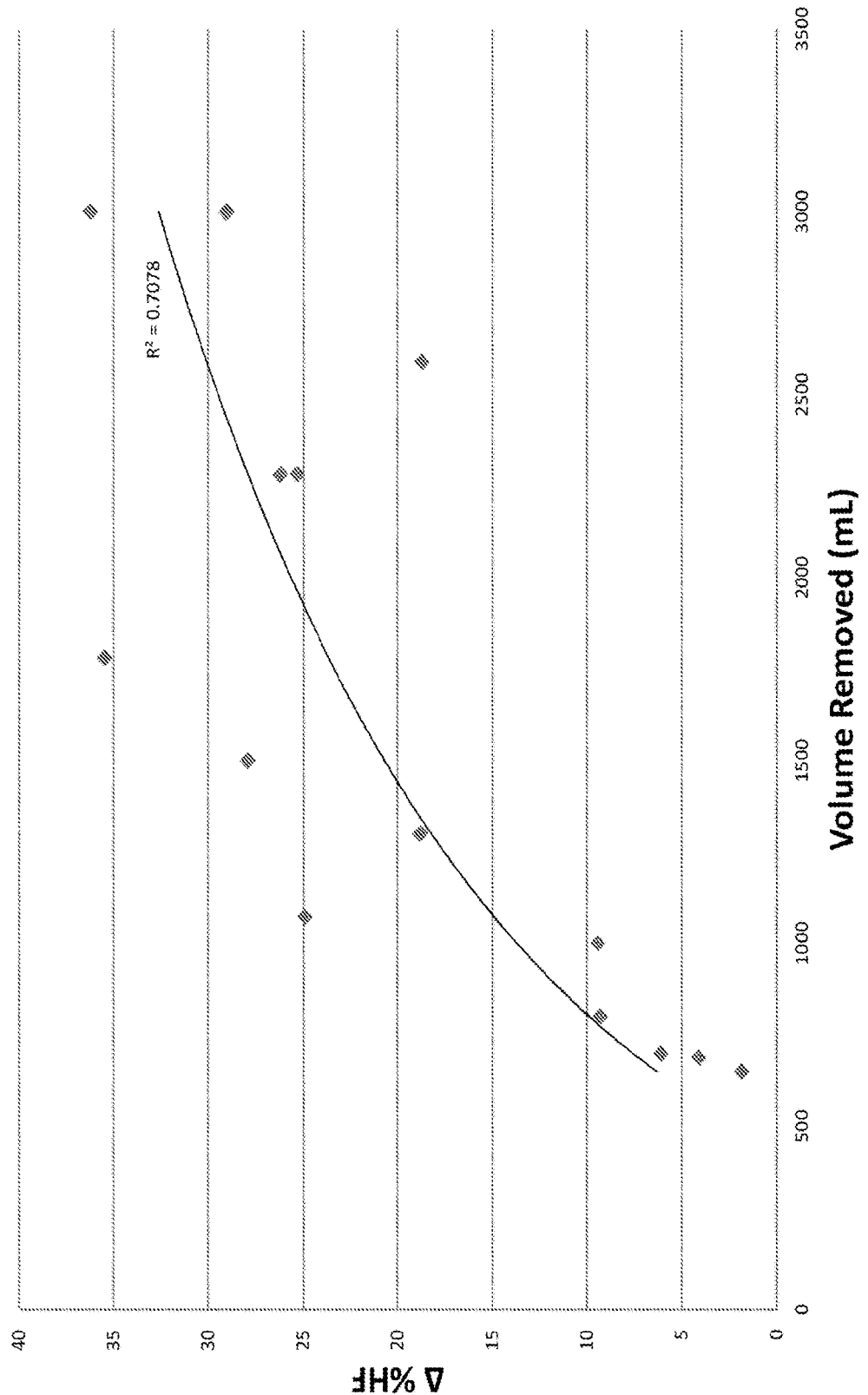
FIG. 11 shows the relationship of $\Delta\%$ HF to volume removed from a patient according to certain embodiments of the present invention.

FIG. 11 shows the relationship of Δ % HF (change in high frequency component) to volume removed from a patient according to certain embodiments of the present invention, which shows how the high frequency component is decreased when volume is removed from a patient. As shown in FIG. 11, $R^2=0.71$.

Figure 12:
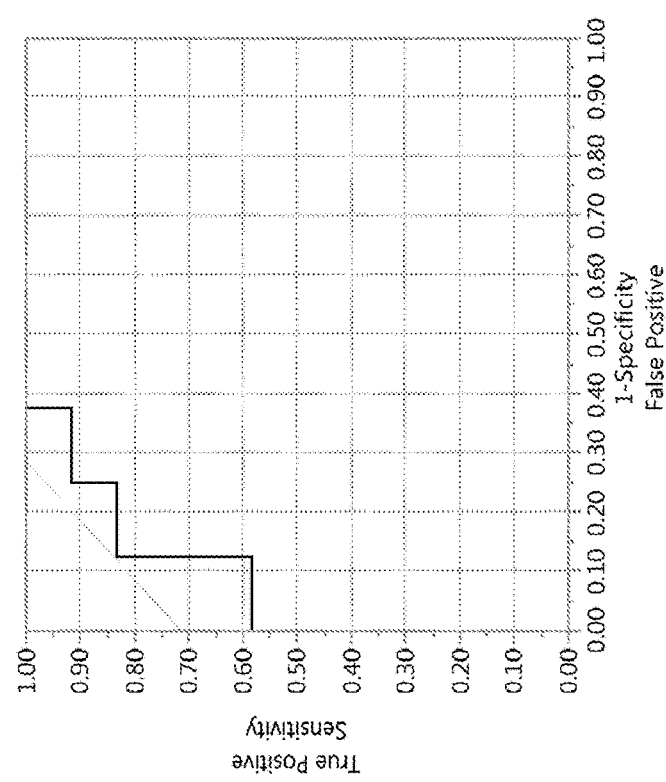
FIG. 12 shows a receiver operator curve (ROC) that demonstrates the ability for non-invasive sensors to predict elevated mean pulmonary artery pressures according to certain embodiments of the present invention.

FIG. 12 shows a receiver operator curve (ROC) that demonstrates the ability for non-invasive sensors to predict elevated mean pulmonary artery pressures according to certain embodiments of the present invention. As shown in FIG. 12, mPAP>25 mmHg, n=20, and AUC=0.92.

Aspects of the invention relate to systems and methods for performing peripheral vascular signal analysis using NIVA, which uses spectral analysis to estimate volume status or other hemodynamic parameters of a living subject, and its applications. In certain aspects, the invention recites, among other things:

1) Peripheral vascular pressure waveform analysis algorithm.
2) Method of measuring peripheral vascular pressure changes and performing spectral analysis for determination of real-time volume status.
3) A peripheral vascular pressure monitor algorithm that can distinguish between euvolemia and hypervolemia (all current technologies stop at euvolemia).
4) A method for assessing volume status in a spontaneously breathing as well as a mechanically ventilated patient.
5) A volume status monitor that uses a peripheral IV or non-invasive vascular monitor.
6) A closed loop system for controlling volume status with a peripheral vascular pressure monitor and intravenous fluid or medication delivery system.

Among other things, the non-invasive device and the NIVA system as disclosed in certain embodiments of the present invention will gain a great deal of military, clinical and consumer significance. The military needs a robust point-of-care method for early hemorrhage detection in the wounded soldier. This device is rugged, wireless, lightweight and wearable with minimal, self-contained energy requirements, conducive to austere environments. The intuitive design and user-friendly interface of the non-invasive device may obviate the need for sophisticated medical training, often not immediately available in the field. Prototype development focuses on a non-invasive wearable wristband based device. This provides early remote volume status and hemorrhage detection and decision-support for wounded soldiers prior to hemodynamic collapse and end organ damage for improved survival.

Further, the non-invasive device and the NIVA system as disclosed in certain embodiments of the present invention will also be of pediatric significance. Venous access is problematic in the pediatric population, and the non-invasive approach would represent a self-contained wearable devise for hemodynamic monitoring of pediatric subjects and other patient populations.

The non-invasive device, and system and method as disclosed in certain embodiments of the present invention may be useful for both the spontaneously breathing and mechanically ventilated patient. Current volume status monitors require mechanical ventilation to detect intravascular volume depletion. However, in multiple settings, patients are often not mechanically ventilated. In comparison, the non-invasive device to detect volume status does not depend on intrathoracic pressure changes for accurate determination of volume status and is therefore suited for the spontaneously breathing patient. This offers a significant advantage over arterial-based devices that analyze Stroke Volume Variations (SVV) and Pulse Pressure Variations (PPV).

Specifically, accurate, intuitive, point-of-care technology is essential for hydration monitoring, hemorrhage detection and goal-directed fluid resuscitation. Appropriate goal-directed fluid therapy preserves end-organ function, improves survival, and conserves medical supplies in the field. Currently there is no non-invasive invasive technology available to monitor volume status. Unguided resuscitation often leads to over-delivery of fluid and associated morbidity and mortality. Based on our preliminary data, our device can detect euvolemia, minimizing the risk for fluid overload. The proposed mobile version of our current device provides a superior POC guide to detect volume status especially for resuscitation to improve survival of the injured person.

Real time monitoring and algorithm-based decision support is essential for timely triage and management of injured personnel. In one embodiment, the device displays volume status data directly in another embodiment it transmits data via Bluetooth technology to Smartphones for real-time graphical display of volume status of the patient. Personnel data can be transferred to cloud-based servers for centralized healthcare guidance and telemedicine option allowing for early interventions and off-loading tasks from field medics.

There remains a need for improved continuity of care for patients. In the combat or trauma setting, there may be multiple transfers of a wounded soldier or patient to various medical centers. The patient currently arrives at the hospital with only a verbal 'handover' from the field. The device or mobile application stores the patient's intravascular volume status along with other physiological variables in a cloud-based server providing graphically display throughout the entire resuscitation history accessible to all providers throughout the continuum of care. Continuous display of the patient's intravascular volume status at the receiving hospital while the patient is en route allows for adequate team and supply preparation in advance of the patient's arrival.

In addition, according to the invention, a non-invasive peripheral vascular analysis device offers substantial advantages over existing hemodynamic monitors for determining volume status.

These characteristics of cost-effective, minimal energy requirements and user-friendly interface are particularly advantageous to civilian trauma patients, pediatric patients, underserved populations, and global health settings.

In certain embodiments, the features of detecting volume changes in mechanically ventilated and spontaneously breathing patients are a significant advancement over current arterial-based technology that depends on intrathoracic changes via positive pressure ventilation in order to detect hypovolemia.

In certain embodiments, the device is the first non-invasive monitor used to guide large-volume resuscitation. Currently determination of euvolemia and hypervolemia require invasive intravascular monitoring which is not feasible in the trauma or pre-hospital setting and puts patients at risk for vascular injury and catheter-based infections.

In addition, development of the device and mobile application can facilitate transfer and storage of real time patient information, allowing receiving hospital can adequately prepare for damage control surgery and resuscitation prior to patient arrival.

Further, automated decision support enhances patient care in global and pre-hospital settings where invasive monitoring and skilled medical personnel may not be immediately available.

In certain embodiments, the NIVA system, device and method as described above may be implement in a variety of applications. For example, one further aspect of the present invention may relate to a system, which includes the NIVA system as described above, and an administration device communicatively connected to the NIVA system, for controlling, based on the at least one hemodynamic parameter of the living subject provided by the NIVA system, administration of a drug or fluid to the living subject, or for controlling a rate or ultrafiltration of fluid removal from the living subject. For example, the administration device may be an IV device, which includes an IV pump for controlling the administration the drug or fluid. In certain embodiments, the administration device is configured to control the administration of the drug or fluid to the living subject based on the at least one hemodynamic parameter of the living subject to maintain a specific physiological condition of the living subject. For example, one particular physiological condition may be euvolemia, and the controlling of the administration of fluid or drug may be conducted to prevent over-resuscitation.

In summary, there is a critical unmet need for a cost effective point of care device for hemorrhage detection, goal-directed resuscitation, and appropriate triage of the wounded person to improve mortality in the casualty care setting. Based on the inventors' studies in a porcine animal model, it has been shown that venous waveform analysis is far more sensitive than standard vital sign monitoring for detecting hemorrhage ranging from subclinical to hypovolemic shock. On the other extreme, it has been shown that vascular waveform analysis is more sensitive than standard vital sign and arterial-based monitoring methods for detecting excessive fluid administration. Thus, the invention has been evolved from an intravascular to non-invasive desktop analysis of venous waveforms.

Extensions for the use of this device include monitoring for dehydration. Preliminary experiments have been performed with acute exercise and have shown that non-invasive vascular waveform analysis detects decreases in intravascular volume associated with strenuous exertion. Thus, such a device could be extremely useful for optimizing physical conditioning of the soldier under austere environmental conditions. Further, the device and platform can be expanded to measure additional vital parameters such as heart and respiratory rates and temperature to assist in the clinical evaluation of wounded, septic or trauma patients.

The inventors have identified a subset of patients who undergo preoperative autologous blood donation in a titrated manner. This environment provides us an excellent opportunity for comparing our non-invasive device with known hemorrhage rate and quantity, invasive hemodynamic monitoring, and echocardiographic imaging. This situation is ideal for algorithm determination and optimization across diverse patient demographics and ongoing resuscitation.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LISTING OF REFERENCES

[1]. Hubetamann B, Lefering R, Taeger G, et al., *Influence of prehospital fluid resuscitation on patients with multiple injuries in hemorrhagic shock in patients from the DGU trauma registry*. Journal of emergencies, trauma, and shock 2011; 4:465-71.

[2]. Holcomb J B, McMullin N R, Pearse L, et al., *Causes of death in U.S. Special Operations Forces in the global war on terrorism: 2001-2004*. Annals of surgery 2007; 245:986-91.

[3]. Eastridge B J, Hardin M, Cantrell J, et al., *Died of wounds on the battlefield: causation and implications for improving combat casualty care*. The Journal of trauma 2011; 71:S4-8.

[4]. Swaroop M, Straus D C, Agubuzu O, Esposito T J, Schermer C R, Crandall M L. *Pre-hospital transport times and survival for Hypotensive patients with penetrating thoracic trauma*. Journal of emergencies, trauma, and shock 2013; 6:16-20.

[5]. Riskin D J, Tsai T C, Riskin L, et al., *Massive transfusion protocols: the role of aggressive resuscitation versus product ratio in mortality reduction*. Journal of the American College of Surgeons 2009; 209:198-205.

[6]. Duke M D, Guidry C, Guice J, et al., *Restrictive fluid resuscitation in combination with damage control resuscitation: time for adaptation*. The journal of trauma and acute care surgery 2012; 73:674-8.

[7]. Paladino L, Sinert R, Wallace D, Anderson T, Yadav K, Zehtabchi S., *The utility of base deficit and arterial lactate in differentiating major from minor injury in trauma patients with normal vital signs*. Resuscitation 2008; 77:363-8.

[8]. Convertino V A. *Blood pressure measurement for accurate assessment of patient status in emergency medical settings*. Aviation, space, and environmental medicine 2012; 83:614-9.

[9]. Convertino V A, Ryan K L, Rickards C A, et al. *Physiological and medical monitoring for en route care of combat casualties*. The Journal of trauma 2008; 64:S342-53.

[10]. Gutierrez G, Reines H D, Wulf-Gutierrez M E. *Clinical review: hemorrhagic shock*. Critical care 2004; 8:373-81.

[11]. Cocchi M N, Kimlin E, Walsh M, Donnino M W. *Identification and resuscitation of the trauma patient in shock*. Emergency medicine clinics of North America 2007; 25:623-42, vii.

[12]. Parks J K, Elliott A C, Gentilello L M, Shafi S. *Systemic hypotension is a late marker of shock after trauma: a validation study of Advanced Trauma Life Support principles in a large national sample*. American journal of surgery 2006; 192:727-31.

[13]. Vandromme M J, Griffin R L, Weinberg J A, Rue L W, 3rd, Kerby J D. *Lactate is a better predictor than systolic blood pressure for determining blood requirement and mortality: could prehospital measures improve trauma triage?* Journal of the American College of Surgeons 2010; 210:861-7, 7-9.

[14]. Marik P E, Monnet X, Teboul J L. *Hemodynamic parameters to guide fluid therapy*. Annals of intensive care 2011; 1:1.

[15]. Desebbe O, Cannesson M. *Using ventilation-induced plethysmographic variations to optimize patient fluid status*. Current opinion in anaesthesiology 2008; 21:772-8.

[16]. Marik P E, Cavallazzi R, Vasu T, Hirani A. *Dynamic changes in arterial waveform derived variables and fluid responsiveness in mechanically ventilated patients: a systematic review of the literature*. Critical care medicine 2009; 37:2642-7.

[17]. Teboul J L, Monnet X. *Prediction of volume responsiveness in critically ill patients with spontaneous breathing activity*. Current opinion in critical care 2008; 14:334-9.

[18]. Cotton B A, Guy J S, Morris J A, Jr., Abumrad N N. *The cellular, metabolic, and systemic consequences of aggressive fluid resuscitation strategies*. Shock 2006; 26:115-21.

[19]. Hussmann B, Lefering R, Waydhas C, et al. *Does increased prehospital replacement volume lead to a poor clinical course and an increased mortality? A matched-pair analysis of 1896 patients of the Trauma Registry of the German Society for Trauma Surgery who were managed by an emergency doctor at the accident site*. Injury 2013; 44:611-7.

[20]. Beecher H K. *Preparation of Battle Casualties for Surgery*. Annals of surgery 1945; 121:769-92.

[21]. Khoury, et al. *Ambulatory monitoring of congestive heart failure by multiple bioelectric impedance vectors*. JACC. 2009 Mar. 24, 53(12): 1075-81.

What is claimed is:

1. A non-invasive vascular analysis (NIVA) system, comprising:
at least one sensor, configured to acquire, for a time period from $T_0$ to $T_2$, vascular signals from at least one peripheral vein, artery or perfused tissue of a living subject, wherein the time period is divided into a first time period from $T_0$ to $T_1$ and a second time period from $T_1$ to $T_2$, wherein the at least one sensor comprises a piezoelectric sensor, a resistive pressure/force sensor, a tonometer, an ultrasound sensor, a bioimpedance sensor, or a pressure transducer and is configured to acquire the vascular signals while positioned externally to the living subject; and a processing device communicatively coupled to the at least one sensor, configured to receive the vascular signals transmitted from the at least one sensor, and perform a spectral analysis on the vascular signals, wherein the spectral analysis comprises the steps of:

processing the vascular signals acquired at the first time period to obtain a first peripheral vascular signal frequency spectrum;

obtaining a plurality of baseline peaks $\{B_{N-1}\}$ on the first peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;

processing the vascular signals acquired at the second time period to obtain a second peripheral vascular signal frequency spectrum;

obtaining a plurality of peaks $\{P_{N-1}\}$ on the second peripheral vascular signal frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining whether hypovolemia or hypervolemia is present within the living subject by determining whether at least one amplitude of the peaks $\{P_{N-1}\}$ differs by more than a threshold amount when compared to a corresponding amplitude of the baseline peaks $\{B_{N-1}\}$.

2. The system of claim 1, wherein the vascular signals are processed by a spectral fast Fourier transform (FFT) analysis to obtain the first peripheral vascular signal frequency spectrum and the second peripheral vascular signal frequency spectrum.

3. The system of claim 1, wherein the at least one sensor and the processing device form a non-invasive device, wherein the non-invasive device is a wearable band, an adhesive, or an attachment being in contact with a surface of skin of the living subject overlying the at least one peripheral vein, artery or perfused tissue.

4. The system of claim 3, wherein the processing device comprises:

a processor configured to receive vascular signals transmitted from the at least one sensor, wherein the at least one sensor and the processor form the non-invasive device; and a monitoring device configured to communicate with the processor to receive vascular signals, and to perform the spectral analysis for monitoring a condition of the living subject.

5. The system of claim 4, wherein the monitoring device is further configured to display results of the spectral analysis on the non-invasive device.

6. The system of claim 4, wherein the monitoring device is configured to communicate with the processor via a wireless protocol, and is a smartphone, a tablet computing device, a laptop computing device, a desktop computing device, or any combination thereof.

7. The system of claim 1, wherein:

the plurality of peaks $\{P_{N-1}\}$ comprises a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$;

the first peak $P_0$ corresponding to the first frequency $F_0$ is associated with a respiratory rate of the living subject;

the second peak $P_1$ corresponding to the second frequency $F_1$ is associated with a heart rate of the living subject; and the third peak $P_2$ corresponding to the third frequency $F_2$ and the fourth peak $P_3$ corresponding to the fourth frequency $F_3$ are associated with harmonics of the living subject.

8. The system of claim 1, further comprising:

an administration device configured to control, based on the determining whether hypovolemia or hypervolemia is present within the living subject, administration of a drug or fluid to the living subject, or a rate or ultrafiltration of fluid removal from the living subject.

9. The system of claim 8, wherein the administration device comprises an intravenous (IV) pump for controlling the administration of the drug or fluid.

10. The system of claim 1, wherein the at least one sensor comprises a piezoelectric sensor.

11. A non-transitory computer readable medium storing instructions that, when executed by a non-invasive vascular analysis (NIVA) system, cause the system to perform functions comprising:

processing vascular signals acquired by at least one sensor during a first time period $T_0$ to $T_1$ to obtain a first peripheral vascular signal frequency spectrum, wherein the at least one sensor comprises a piezoelectric sensor, a resistive pressure/force sensor, a tonometer, an ultrasound sensor, a bioimpedance sensor, or a pressure transducer and is configured to acquire the vascular signals while positioned externally to the living subject;

obtaining a plurality of baseline peaks $\{B_{N-1}\}$ on the first peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;

processing vascular signals acquired by the at least one sensor at a second time period $T_1$ to $T_2$ that follows the first time period to obtain a second peripheral vascular signal frequency spectrum;

obtaining a plurality of peaks $\{P_{N-1}\}$ on the second peripheral vascular signal frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and determining whether hypovolemia or hypervolemia is present within the living subject by determining whether at least one amplitude of the peaks $\{P_{N-1}\}$ differs by more than a threshold amount when compared to a corresponding amplitude of the baseline peaks $\{B_{N-1}\}$.

12. The non-transitory computer readable medium of claim 11, wherein the vascular signals are processed by a spectral fast Fourier transform (FFT) analysis to obtain the first peripheral vascular signal frequency spectrum and the second peripheral vascular signal frequency spectrum.

13. The non-transitory computer readable medium of claim 11, the functions further comprising displaying results of the determining whether hypovolemia or hypervolemia is present within the living subject.

14. The non-transitory computer readable medium of claim 11, wherein:
the plurality of peaks $\{P_{N-1}\}$ comprises a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$;
the first peak $P_0$ corresponding to the first frequency $F_0$ is associated with a respiratory rate of the living subject;
the second peak $P_1$ corresponding to the second frequency $F_1$ is associated with a heart rate of the living subject; and
the third peak $P_2$ corresponding to the third frequency $F_2$ and the fourth peak $P_3$ corresponding to the fourth frequency $F_3$ are associated with harmonics of the living subject.

15. The non-transitory computer readable medium of claim 11, wherein the at least one sensor comprises a piezoelectric sensor.

16. A method comprising:
processing vascular signals acquired by at least one sensor during a first time period $T_0$ to $T_1$ to obtain a first peripheral vascular signal frequency spectrum, wherein the at least one sensor comprises a piezoelectric sensor, a resistive pressure/force sensor, a tonometer, an ultrasound sensor, a bioimpedance sensor, or a pressure transducer and is configured to acquire the vascular signals while positioned externally to the living subject;
obtaining a plurality of baseline peaks $\{B_{N-1}\}$ on the first peripheral vascular signal frequency spectrum, wherein N is a positive integer, and the plurality of baseline peaks $\{B_{N-1}\}$ respectively corresponds to a plurality of frequencies $\{F_0, F_1, \ldots, F_N\}$, such that $B_{N-1}$ is a function of $F_{N-1}$ satisfying $B_{N-1}=B_{N-1}(F_{N-1})$, wherein $F_N$ is greater than $F_{N-1}$;
processing vascular signals acquired by the at least one sensor at a second time period $T_1$ to $T_2$ that follows the first time period to obtain a second peripheral vascular signal frequency spectrum;
obtaining a plurality of peaks $\{P_{N-1}\}$ on the second peripheral vascular signal frequency spectrum, wherein the plurality of peaks $\{P_{N-1}\}$ correspond to the plurality of frequencies $\{F_0, F_1, \ldots, F_N\}$, such that $P_{N-1}$ is a function of $F_{N-1}$ satisfying $P_{N-1}=P_{N-1}(F_{N-1})$; and
determining whether hypovolemia or hypervolemia is present within the living subject by determining whether at least one amplitude of the peaks $\{P_{N-1}\}$ differs by more than a threshold amount when compared to a corresponding amplitude of the baseline peaks $\{B_{N-1}\}$.

17. The method of claim 16, wherein the vascular signals are processed by a spectral fast Fourier transform (FFT) analysis to obtain the first peripheral vascular signal frequency spectrum and the second peripheral vascular signal frequency spectrum.

18. The method of claim 16, wherein the at least one sensor and the processing device form a non-invasive device, wherein the non-invasive device is a wearable band, an adhesive, or an attachment being in contact with a surface of skin of the living subject overlying the at least one peripheral vein, artery or perfused tissue.

19. The method of claim 16, further comprising displaying results of the determining whether hypovolemia or hypervolemia is present within the living subject.

20. The method of claim 16, wherein:
the plurality of peaks $\{P_{N-1}\}$ comprises a first peak $P_0$ corresponding to a first frequency $F_0$, a second peak $P_1$ corresponding to a second frequency $F_1$, a third peak $P_2$ corresponding to a third frequency $F_2$ and a fourth peak $P_3$ corresponding to a fourth frequency $F_3$;
the first peak $P_0$ corresponding to the first frequency $F_0$ is associated with a respiratory rate of the living subject;
the second peak $P_1$ corresponding to the second frequency $F_1$ is associated with a heart rate of the living subject; and
the third peak $P_2$ corresponding to the third frequency $F_2$ and the fourth peak $P_3$ corresponding to the fourth frequency $F_3$ are associated with harmonics of the living subject.

21. The method of claim 16, further comprising controlling, based on the determining whether hypovolemia or hypervolemia is present within the living subject, administration of a drug or fluid to the living subject, or a rate or ultrafiltration of fluid removal from the living subject.

22. The method of claim 16, wherein the at least one sensor comprises a piezoelectric sensor.

* * * * *